(12) United States Patent
Rabindran et al.

(10) Patent No.: US 11,679,499 B2
(45) Date of Patent: *Jun. 20, 2023

(54) SYSTEMS AND METHODS FOR CONTROLLING A ROBOTIC MANIPULATOR OR ASSOCIATED TOOL

(71) Applicant: Intuitive Surgical Operations, Inc., Sunnyvale, CA (US)

(72) Inventors: Dinesh Rabindran, San Jose, CA (US); Simon P. DiMaio, San Carlos, CA (US); Kollin M. Tierling, Los Altos Hills, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/493,918

(22) Filed: Oct. 5, 2021

(65) Prior Publication Data

US 2022/0080591 A1    Mar. 17, 2022

Related U.S. Application Data

(63) Continuation of application No. 16/185,687, filed on Nov. 9, 2018, now Pat. No. 11,161,243.

(Continued)

(51) Int. Cl.
*B25J 9/16* (2006.01)
*A61B 34/37* (2016.01)

(52) U.S. Cl.
CPC .............. *B25J 9/1653* (2013.01); *A61B 34/37* (2016.02); *B25J 9/1607* (2013.01); *B25J 9/1641* (2013.01);

(Continued)

(58) Field of Classification Search
CPC .............................. B25J 9/1653; B25J 9/1664
See application file for complete search history.

(56) References Cited

U.S. PATENT DOCUMENTS 6,995,536 B2    2/2006 Challoner
8,004,229 B2    8/2011 Nowlin et al.
(Continued)

OTHER PUBLICATIONS

Axelsson P. et al., "H∞-Controller Design Methods Applied to One Joint of a Flexible Industrial Manipulator," 19th IFAC World Congress Cape Town, South Africa, Aug. 24-29, 2014, pp. 210-216.

(Continued)

*Primary Examiner* — Kira Nguyen
(74) *Attorney, Agent, or Firm* — Haynes and Boone, LLP

(57) ABSTRACT

A system includes a robotic manipulator including a serial chain comprising a first joint, a second joint, and a first link. The system further includes a processing unit including one or more processors. The processing unit is configured to receive first link data from a first sensor system located at the first link, generate a first joint state estimate of the first joint based on the first link data, and generate a second joint state estimate of the second joint. The processing unit is further configured to apply a first weight to the first joint state estimate to generate a first weighted joint state estimate, apply a second weight to the second joint state estimate to generate a second weighted joint state estimate, and control the first and second joints based on the first weighted joint state estimate and second weighted joint state estimate.

20 Claims, 14 Drawing Sheets

Related U.S. Application Data

(60) Provisional application No. 62/584,206, filed on Nov. 10, 2017.

(52) U.S. Cl.
CPC ........... *B25J 9/1664* (2013.01); *B25J 9/1689* (2013.01); *B25J 9/1694* (2013.01); *G05B 2219/37388* (2013.01)

(56) References Cited

U.S. PATENT DOCUMENTS

| | | |
|---|---|---|
| 8,541,970 B2 | 9/2013 | Nowlin et al. |
| 8,624,537 B2 | 1/2014 | Nowlin et al. |
| 8,749,189 B2 | 6/2014 | Nowlin et al. |
| 8,749,190 B2 | 6/2014 | Nowlin et al. |
| 8,786,241 B2 | 7/2014 | Nowlin et al. |
| 8,816,628 B2 | 8/2014 | Nowlin et al. |
| 8,823,308 B2 | 9/2014 | Nowlin et al. |
| 9,510,911 B2 | 12/2016 | Hourtash |
| 9,554,859 B2 | 1/2017 | Nowlin et al. |
| 9,821,459 B2 * | 11/2017 | Naitou .................. B25J 13/085 |
| 11,161,243 B2 | 11/2021 | Rabindran et al. |
| 11,173,597 B2 | 11/2021 | Rabindran et al. |
| 2006/0265120 A1 | 11/2006 | Coleman et al. |
| 2007/0057842 A1 | 3/2007 | Coleman et al. |
| 2007/0156019 A1 | 7/2007 | Larkin et al. |
| 2007/0156122 A1 | 7/2007 | Cooper |
| 2009/0326556 A1 | 12/2009 | Diolaiti et al. |
| 2014/0009100 A1 | 1/2014 | Sera |
| 2014/0052152 A1 | 2/2014 | Au et al. |
| 2014/0277741 A1 | 9/2014 | Kwon et al. |
| 2014/0316431 A1 * | 10/2014 | Hourtash ............... A61B 34/37 606/130 |
| 2014/0358161 A1 * | 12/2014 | Hourtash ............... B25J 9/1607 901/15 |
| 2015/0032126 A1 | 1/2015 | Nowlin et al. |
| 2015/0120053 A1 | 4/2015 | Motoyoshi |
| 2015/0374446 A1 * | 12/2015 | Malackowski ........ A61B 34/10 606/130 |
| 2016/0030119 A1 * | 2/2016 | Devengenzo .......... A61B 34/37 606/130 |
| 2016/0301845 A1 | 10/2016 | Bell et al. |
| 2019/0000576 A1 | 1/2019 | Mintz et al. |
| 2019/0143506 A1 | 5/2019 | Rabindran et al. |
| 2019/0328475 A1 | 10/2019 | Arai et al. |

OTHER PUBLICATIONS

Behi F., et al., "Parametric Identification for Industrial Manipulators Using Experimental Modal Analysis," IEEE Transactions on Robotics and Automation, vol. 7 (5), Oct. 1991, pp. 642-652.

Chen W., et al., "Direct Joint Space State Estimation in Robots with Multiple Elastic Joints," IEEE/ASME Transactions on Mechatronics, Apr. 2014, vol. 19 (2), pp. 697-706.

Kim et al., "An Ultrasound Robotic System Using the Commercial Robot UR5," Frontiers in Robotics and AI, Feb. 2016, vol. 3, pp. 1-16.

Olsson F., et al., "Experimental Evaluation of Joint Position Estimation Using Inertial Sensors," 20th International Conference on Information Fusion, Jul. 2017, pp. 1-8.

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

Vikas V., et al., "Joint Angle Measurement Using Strategically Placed Accelerometers and Gyroscope," Journal of Mechanisms and Robotics, Transactions of the ASME, vol. 8, May 2016, pp. 021003-1-021003-7.

* cited by examiner

SYSTEMS AND METHODS FOR CONTROLLING A ROBOTIC MANIPULATOR OR ASSOCIATED TOOL

CROSS-REFERENCE TO RELATED APPLICATIONS

This application is a Continuation of U.S. patent application Ser. No. 16/185,687, filed Oct. 9, 2018, which claims priority to and the benefit of U.S. Provisional Application 62/584,206 filed Nov. 10, 2017, which is incorporated by reference herein in their entireties.

FIELD

The present disclosure is directed to systems and methods for performing a robotic procedure, and more particularly to systems and methods for controlling more particularly to systems and methods for controlling a robotic manipulator or a tool associated with a robotic manipulator.

BACKGROUND

Robotic manipulator assemblies can be operated to control motion of tools in a workspace. For example, such robotic manipulators can be used to perform non-medical and medical procedures. As a specific example, teleoperated surgical manipulators can be used to perform minimally invasive medical procedures.

It is desirable in medical techniques are intended to reduce the amount of tissue that is damaged during medical procedures, thereby reducing patient recovery time, discomfort, and harmful side effects. For example, minimally invasive techniques may be performed through natural orifices in a patient anatomy or through one or more incisions. Through these natural orifices or incisions, clinicians may insert medical tools to reach a target tissue location. Minimally invasive medical tools include tools such as therapeutic tools, diagnostic tools, and surgical tools. Minimally invasive medical tools may also include imaging tools such as endoscopic tools that provide a user visualization within the patient anatomy.

Robotic manipulators may be teleoperated or otherwise computer-assisted. For example, a tool may be held by a robotic manipulator assembly for performing a procedure. However, flexibility in such a robotic manipulator assembly and the tool may cause under-damped vibrations with undesirably long settling times. Flexibility (compliance) may be used to measure physical compliance, mechanical compliance, structural compliance, and the ability to deflect under load. In examples where the robotic manipulator assembly (including its base, joints, and links) has a relatively large flexibility and/or has relatively large link masses or inertias (e.g., greater than corresponding thresholds of flexibility/link masses/inertias), motions commanded of the robotic manipulator assembly or external disturbances may cause such vibrations. As such, a combination of physical parameters including compliance (e.g., physical, mechanical, and structural compliance), damping (e.g., physical damping including viscous damping, where viscous damping elements (e.g., lubricant friction or structural damping) resist motion with forces proportional to the velocity of motion), and mass/inertia results in a low mechanical resonance with less than desired damping. During a procedure, commanded motions or external disturbances may excite these low mechanical resonances causing undesirable vibrations. While performing a procedure, such vibrations experienced at the tool tip or another point of control on the robot manipulator may result in inferior system performance. For example, such vibrations may make it difficult for the computer-assisted system to achieve or follow commanded trajectories for the tool.

Such vibrations may negatively affect control in all types of robotic systems, including medical robotic systems. In a medical robotic example, such vibrations may make it difficult for a medical robotic system to perform the commanded manipulations of tissue, movement of imaging systems such as endoscopes and ultrasonic probes, insertion of needles, application of sutures, etc. For a further example, in some implementations, the tool is moved around a remote center of motion (also referred to as "remote center") during part or all of a procedure. In some instances, the vibrations may cause the remote center of motion to move during surgery imparting undesirable forces on the body wall at the port of entry. The vibrations may cause the actual pose or motion of the tool (or a manipulator holding the tool) to deviate from the commanded posed or motion to such an extent that the tool (or manipulator) acts as if the remote center has moved beyond a predetermined tolerance from its defined position. That is, the range of location of the virtual fulcrum associated with the motion of the manipulator and/or the tool is caused by the vibrations to exceed a tolerance amount from a defined remote center of motion.

Thus, systems and methods are desired to provide better control of robotic systems, such as better control of a manipulator of a robotic system by mitigating undesirable vibrations, better control of the tip of a tool held by the robotic system (where the tool is a camera or other imaging device, better control of the tip can provide improved image stabilization), and the motion of the manipulator or a tool supported by the manipulator about the remote center of motion of the tool.

SUMMARY

The embodiments of the invention are summarized by the claims that follow below.

In one illustrative embodiment, a system includes a robotic manipulator including a serial chain comprising a first joint, a second joint, and a first link. The system further includes a processing unit including one or more processors. The processing unit is configured to receive first link data from a first sensor system located at the first link, generate a first joint state estimate of the first joint based on the first link data, and generate a second joint state estimate of the second joint. The processing unit is further configured to apply a first weight to the first joint state estimate to generate a first weighted joint state estimate, apply a second weight to the second joint state estimate to generate a second weighted joint state estimate, and control the first and second joints based on the first weighted joint state estimate and second weighted joint state estimate.

In another illustrative embodiment, a method comprises receiving first link data from a first sensor system located at a first link of a robotic manipulator including a serial chain comprising a first joint, a second joint, and the first link. A first joint state estimate of the first joint is generated based on the first link data. A second joint state estimate of the second joint is generated. A first weight is applied to the first joint state estimate to generate a first weighted joint state estimate. A second weight is applied to the second joint state estimate to generate a second weighted joint state estimate.

The first and second joints are controlled based on the first weighted joint state estimate and second weighted joint state estimate.

In another illustrative embodiment, a non-transitory machine-readable medium comprising a plurality of machine-readable instructions which, when executed by one or more processors, are adapted to cause the one or more processors to perform a method. The method comprises receiving first link data from a first sensor system located at a first link of a robotic manipulator including a serial chain comprising a first joint, a second joint, and the first link. A first joint state estimate of the first joint is generated based on the first link data. A second joint state estimate of the second joint is generated. A first weight is applied to the first joint state estimate to generate a first weighted joint state estimate. A second weight is applied to the second joint state estimate to generate a second weighted joint state estimate. The first and second joints are controlled based on the first weighted joint state estimate and second weighted joint state estimate.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

Figure 1A:
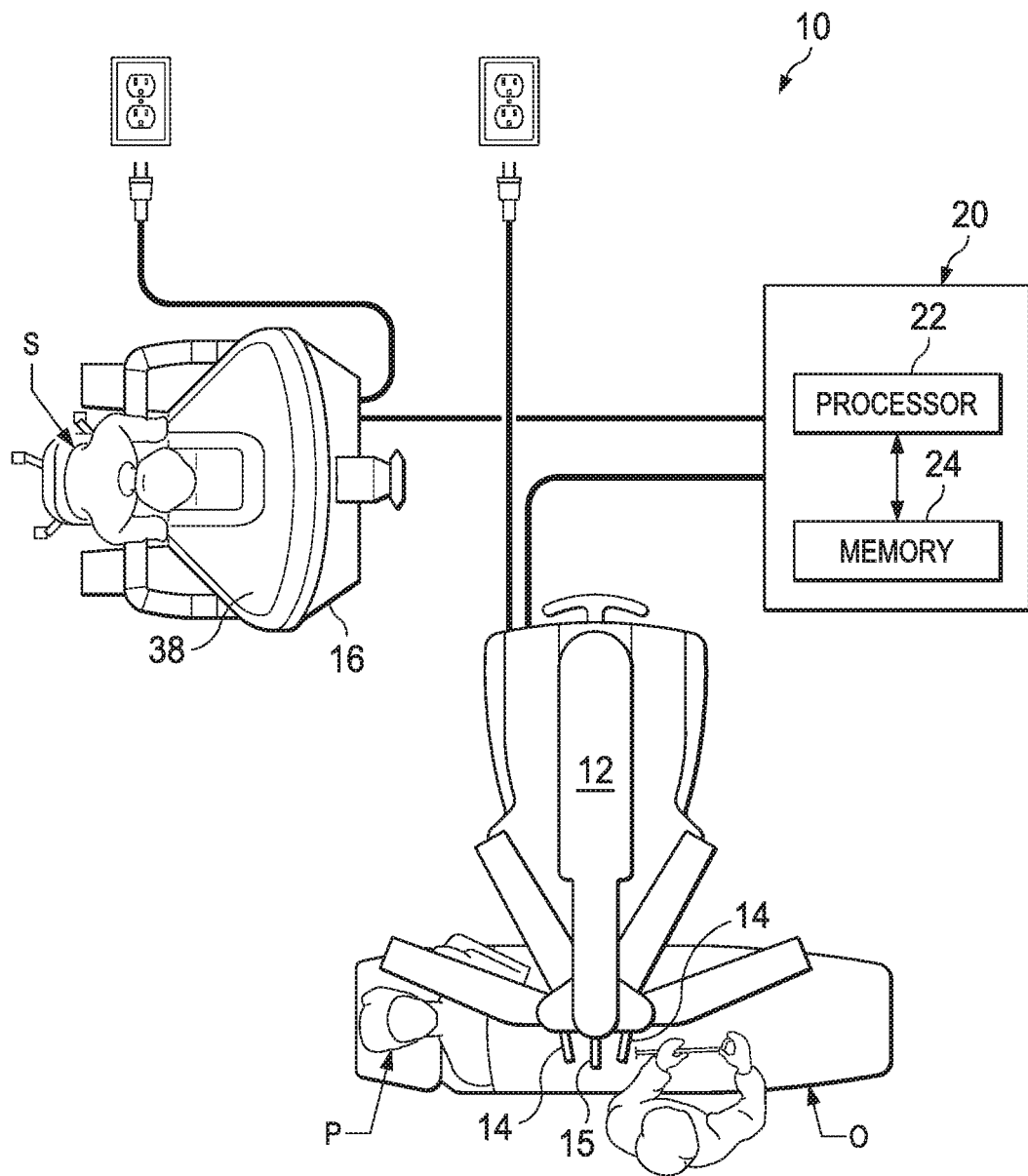
FIG. 1A is a schematic view of a robotic medical system, in accordance with an embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances, well-known methods, procedures, components, and circuits have not been described in detail so as not to unnecessarily obscure aspects of the embodiments of the invention.

Any alterations and further modifications to the described devices, tools, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances, the same reference numbers are used throughout the drawings to refer to the same or like parts.

Although some of the examples described herein often refer to surgical procedures or tools, or medical procedures or tools, the techniques disclosed also apply to non-medical procedures and non-medical tools. For example, the tools, systems, and methods described herein may be used for non-medical purposes including industrial uses, general robotic uses, and sensing or manipulation of non-tissue work pieces. Other example applications involve surgical or non-surgical cosmetic improvements, imaging of or gathering data from human or animal anatomy, training medical or non-medical personnel, performing procedures on tissue removed from human or animal anatomies (without return to a human or animal anatomy), and performing procedures on human or animal cadavers.

In the discussion below, boldface lowercase letters (e.g., a) denote column vectors, and boldface upper case letters (e.g., A) denote matrices. The transpose of a matrix A is denoted as $A^T$. The inverse or pseudo inverse of a matrix A is denoted as $A^{-1}$.

The embodiments below will describe various tools and portions of tools in terms of their state in three-dimensional space. As used herein, the term "position" refers to the location of an object or a portion of an object in a three-dimensional space (e.g., three degrees of translational freedom that can be described using changes in Cartesian X, Y, Z coordinates, such as along Cartesian X, Y, Z axes). As used herein, the term "orientation" refers to the rotational placement of an object or a portion of an object (three degrees of rotational freedom—e.g., which can be described using roll, pitch, and yaw). As used herein, the term "pose" refers to the position of an object or a portion of an object in at least one degree of translational freedom, and to the orientation of that object or that portion of that object in at least one degree of rotational freedom. For an asymmetric, rigid body in a three-dimensional space, a full pose can be described with six parameters in six total degrees of freedom. As used herein, the term "velocity" refers to the first time derivative of pose in general and "acceleration" refers to the second time derivative of pose in general, unless otherwise specified. The term "order" refers to the level of the differentiation with respect to time. For example, velocity is a first order property or signal and acceleration is a second order property or signal. "Higher-order" refers to second or higher order and "lower-order" refers to less than order 2.

As used herein, the term "estimate" of a signal refers to a direct measurement of the signal, or numerical or analytical computation of the signal using different measurements, filtered measurements, and/or a combination thereof. The term "observable" refers to the capability of being estimated. The term "fused" or "fusion" of a plurality of signals refers to combining the plurality of signals, using methods including, for example, arithmetic average, weighted mean, linear or non-linear combination, and Kalman filter with or without the use of additional mathematical models.

Referring to FIG. 1A of the drawings, an example robotic system is shown. Specifically, in FIG. 1A, a computer-aided, robotic medical system that may be teleoperated and used in, for example, medical procedures including diagnostic, therapeutic, or surgical procedures, is generally indicated by the reference numeral 10. As will be described, the teleoperational systems of this disclosure are under the teleoperational control of an operator. In some embodiments, manipulators or other parts of a robotic system may be controlled directly through manual interaction with the manipulators (or the other parts) themselves. Thus, "teleoperated manipulators" as used in this application include manipulators that can be controlled only through teleoperation, and manipulators that can be controlled through teleoperation and through direct manual control. Further, in some embodiments, a non-teleoperational or teleoperational medical system may be under the partial control of a computer programmed to perform the procedure or sub-procedure, and/or assist in the changing of tool and reinsertion of the tool into a patient body. In still other alternative embodiments, a fully automated medical system, under the full control of a computer programmed to perform the procedure or sub-procedure, may be used to perform procedures or sub-procedures, and/or assist in the changing of tool and reinsertion of the tool into a patient body.

As shown in FIG. 1A, the teleoperational medical system 10 generally includes a manipulator assembly 12 mounted to or near an operating table O on which a patient P is positioned. The manipulator assemblies described herein often include one or more robotic manipulators and tools mounted thereon, although the term "manipulator assembly" also encompasses the manipulator without the tool mounted thereon. The manipulator assembly 12 may be referred to as a patient side cart in this example, since it comprises a cart and is designed to be used next to a patient. None, one, or both of the medical tools 14, 15 may include an imaging system. Within this disclosure, when the medical tool 15 includes an imaging system, it may also be referred to as the imaging system 15. The imaging system 15 may comprise an endoscopic imaging system using optical imaging technology, or comprise another type of imaging system using other technology (e.g. ultrasonic, fluoroscopic, etc.). An operator input system 16 allows an operator such as a surgeon or other type of clinician S to view images of or representing the procedure site and to control the operation of the medical tool 14 and/or the medical tool 15.

The operator input system 16 for the teleoperational medical system 10 may be "mechanically grounded" by being connected to a base with linkages such as to an operator's console, or it may be "mechanically ungrounded" and not be thus connected. As shown in FIG. 1A, the operator input system 16 is connected to an operator's console 38 that is usually located in the same room as operating table O during a surgical procedure. It should be understood, however, that the operator S can be located in a different room or a completely different building from the patient P. The operator input system 16 generally includes one or more control device(s) for controlling the medical tool 14. (The operator input system 16 is also referred to herein as "master manipulators" and "master input devices" and "input devices".) The control device(s) may include one or more of any number of a variety of input devices, such as hand grips, joysticks, trackballs, data gloves, trigger-guns, foot pedals, hand-operated controllers, voice recognition devices, touch screens, body motion or presence sensors, and the like. In some embodiments, the control device(s) will be provided with the same degrees of freedom as the medical tools of the robotic assembly to provide the operator with telepresence; that is, the operator is provided with the perception that the control device(s) are integral with the tools so that the operator has a sense of directly controlling tools as if present at the procedure site. In other embodiments, the control device(s) may have more or fewer degrees of freedom than the associated medical tools and still provide the operator with telepresence. In some embodiments, the control device(s) are manual input devices which move with six degrees of freedom, and which may also include an actuatable handle for actuating medical tools (for example, for closing grasping jaw end effectors, applying an electrical potential to an electrode, delivering a medicinal treatment, and the like).

The manipulator assembly 12 supports and manipulates the medical tool 14 while the operator S views the procedure site through the operator's console. An image of the procedure site can be obtained by the medical tool 15, such as via an imaging system comprising a monoscopic or stereoscopic endoscope, which can be manipulated by the manipulator assembly 12 to orient the medical tool 15. An electronics cart can be used to process the images of the procedure site for subsequent display to the operator S through the operator's console. The number of medical tools 14 used at one time will generally depend on the medical diagnostic or treatment (e.g. surgical) procedure and the space constraints within the operating room among other factors. The manipulator assembly 12 may include a kinematic structure of one or more non-servo controlled links (e.g., one or more links that may be manually positioned and locked in place) and a robotic manipulator. The manipulator assembly 12 includes a plurality of motors that drive inputs on the medical tools 14. These motors move in response to commands from the control system (e.g., control system 20). The motors include drive systems which when coupled to the medical tools 14 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the tool for grasping tissue in the jaws of a biopsy device or the like. The medical tools 14 may include end effectors having a single working member such as a scalpel, a blunt blade, a needle, an imaging sensor, an optical fiber, an electrode, etc. Other end effectors may include multiple working members, and examples include forceps, graspers, scissors, clip appliers, staplers, bipolar electrocautery instruments, etc.

The teleoperational medical system 10 also includes a control system 20. The control system 20 includes at least one memory 24 and at least one processor 22, and typically a plurality of processors, for effecting control between the medical tool 14, the operator input system 16, and other auxiliary systems 26 which may include, for example, imaging systems, audio systems, fluid delivery systems, display systems, illumination systems, steering control systems, irrigation systems, and/or suction systems. The control system 20 also includes programmed instructions (e.g., a computer-readable medium storing the instructions) to implement some or all of the methods described in accordance with aspects disclosed herein. While control system 20 is shown as a single block in the simplified schematic of FIG. 1A, the system may include two or more data processing circuits with one portion of the processing optionally being performed on or adjacent the manipulator assembly 12, another portion of the processing being performed at the operator input system 16, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 20 supports wireless communication protocols such as Bluetooth, IrDA, HomeRF, IEEE 802.11, DECT, and Wireless Telemetry.

In some embodiments, the control system 20 may include one or more servo controllers that receive force and/or torque feedback from the medical tool 14 or from the manipulator assembly 12. Responsive to the feedback, the servo controllers transmit signals to the operator input system 16. The servo controller(s) may also transmit signals that instruct the manipulator assembly 12 to move the medical tool(s) 14 and/or 15 which extends into an internal procedure site within the patient body via openings in the body. Any suitable conventional or specialized controller may be used. A controller may be separate from, or integrated with, manipulator assembly 12. In some embodiments, the controller and manipulator assembly are provided as part of an integrated system such as a teleoperational arm cart positioned proximate to the patient's body during the medical procedure.

The control system 20 can be coupled to the medical tool 15 and can include a processor to process captured images for subsequent display, such as to an operator using the operator's console or wearing a head-mounted display system, on one or more stationary or movable monitors near the control system, or on another suitable display located locally and/or remotely. For example, where a stereoscopic endoscope is used, the control system 20 can process the captured images to present the operator with coordinated stereo images of the procedure site. Such coordination can include alignment between the stereo images and can include adjusting the stereo working distance of the stereoscopic endoscope.

In alternative embodiments, the robotic system may include more than one manipulator assembly and/or more than one operator input system. The exact number of manipulator assemblies will depend on the surgical procedure and the space constraints within the operating room, among other factors. The operator input systems may be collocated, or they may be positioned in separate locations. Multiple operator input systems allow more than one operator to control one or more manipulator assemblies in various combinations.

Figure 1B:
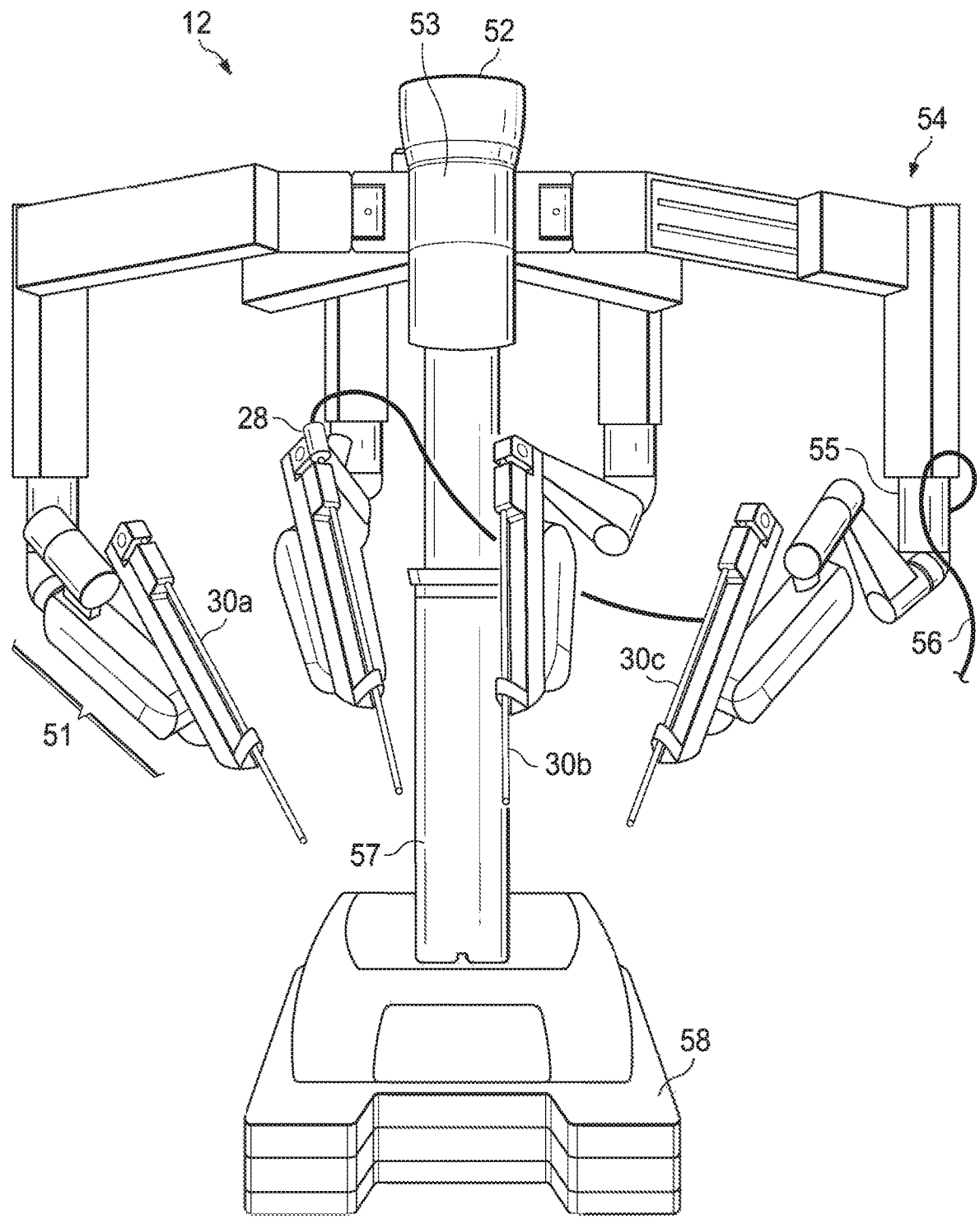
FIG. 1B is a perspective view of a manipulator assembly, in accordance with an embodiment of the present disclosure.

FIG. 1B is a perspective view of one embodiment of a manipulator assembly 12 that is configured in the form of a cart that is located near the patient during a medical procedure. Thus, this manipulator assembly of FIG. 1B may also be referred to as a patient side cart. The manipulator assembly 12 shown provides for the manipulation of three medical tools 30a, 30b, 30c (e.g., medical tools 14) and a medical tool 28 including an imaging device (e.g., medical tool 15), such as a stereoscopic endoscope used for the capture of images of the work piece or of the site of the procedure (also called "work site"). The medical tool 28 may transmit signals over a cable 56 to the control system 20. Manipulation is provided by robotic manipulators having a number of joints. The medical tool 28 and the surgical tools 30a-c can be positioned and manipulated through incisions in, or natural orifices of, the patient so that a kinematic remote center is maintained at the incisions or natural orifices. Images of the work site can include images of the distal ends of the surgical tools 30a-c when they are positioned within the field-of-view of the imaging device of the medical tool 28.

The manipulator assembly 12 includes a moveable, lockable, and drivable base 58. The drivable base 58 is connected to a telescoping column 57, which allows for adjustment of the height of the arms 54 (also called "manipulators 54"). The arms 54 may include a rotating joint 55 that both rotates and translates parallel to the column 57. The arms 54 may be connected to an orienting platform 53. The orienting platform 53 may be capable of 360 degrees of rotation. The manipulator assembly 12 may also include a telescoping horizontal cantilever 52 for moving the orienting platform 53 in a horizontal direction.

In the present example, each of the arms 54 includes a manipulator arm portion 51. The manipulator arm portion 51 may connect directly to a medical tool 14. The manipulator arm portion 51 may be teleoperatable. In some examples, the arms 54 connecting to the orienting platform are not teleoperatable. Rather, such arms 54 are positioned as desired before the operator S begins operation with the teleoperative components.

Endoscopic and other imaging systems (e.g., medical tool 15) may be provided in a variety of configurations, including ones having rigid or flexible structures. Rigid endoscopes include a rigid tube housing a relay lens system for transmitting an image from a distal end to a proximal end of the endoscope. Flexible endoscopes transmit images using one or more flexible optical fibers. Digital image based endoscopes may have a "chip on the tip" design in which a distal digital sensor such as a one or more charge-coupled device (CCD) or a complementary metal oxide semiconductor (CMOS) device store image data. Endoscopic imaging systems may also utilize other imaging techniques such as ultrasonic, infrared, and fluoroscopic technologies. Endoscopic imaging systems may provide two- or three-dimensional images to the viewer. Two-dimensional images may provide limited depth perception. Three-dimensional stereo endoscopic images may provide the viewer with more accurate depth perception. Stereo endoscopic tools employ stereo cameras to capture stereo images of the patient anatomy. An endoscopic tool may be a fully sterilizable assembly with the endoscope cable, handle and shaft all rigidly coupled and hermetically sealed.

Figure 1C:
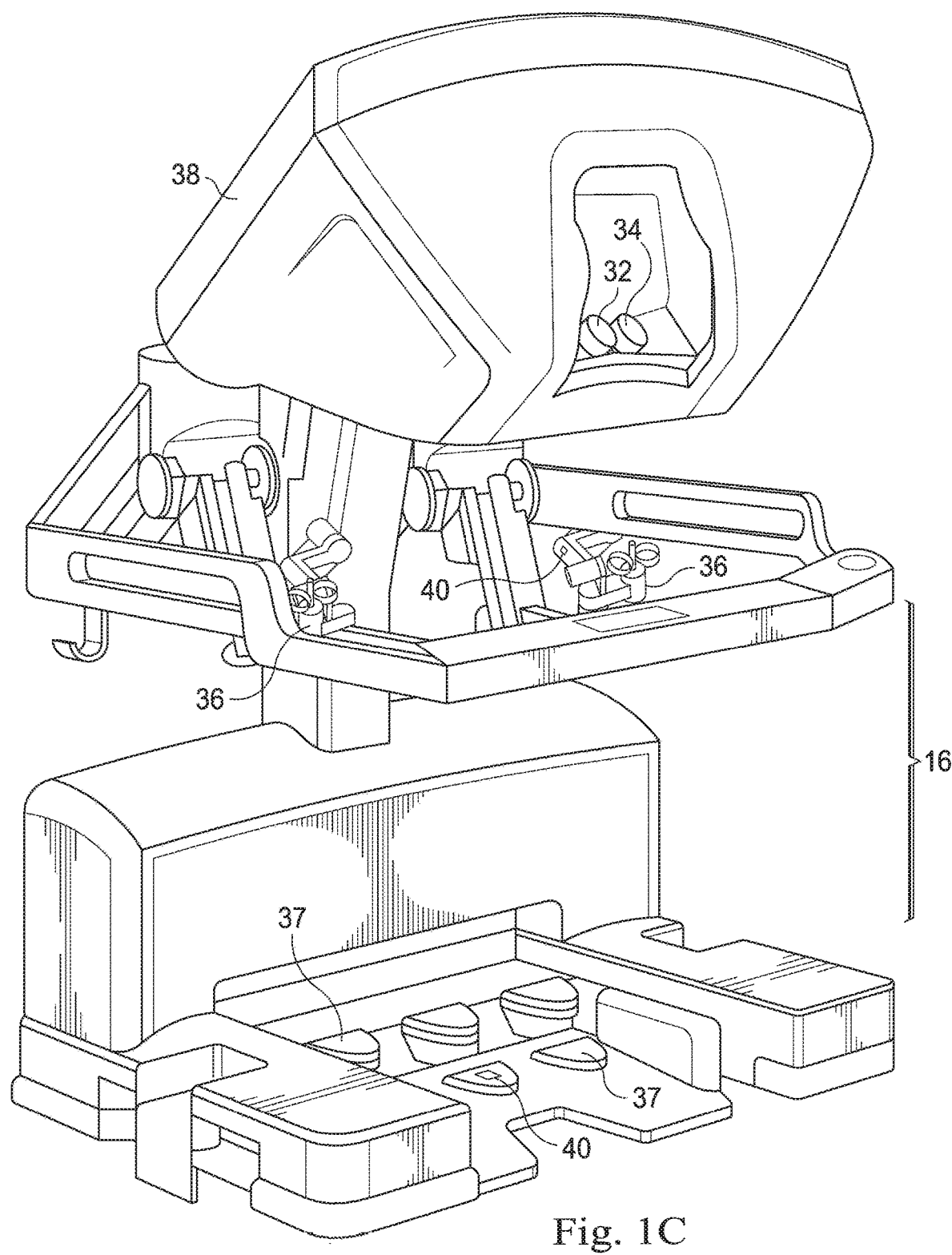
FIG. 1C is a perspective view of an operator's control console for a robotic medical system, in accordance with an embodiment of the present disclosure.

FIG. 1C is a perspective view of the operator's console 38. The operator's console 38 includes a left eye display 32 and a right eye display 34 for presenting the operator S with a coordinated stereo view of the surgical environment that enables depth perception. An operator input system 16 of the operator's console 38 includes one or more input control devices 36, which in turn causes the manipulator assembly 12 to manipulate one or more medical tools 14 and/or 15. The input control devices 36 may be used to, for example, close grasping jaw end effectors, apply an electrical potential to an electrode, deliver a medicinal treatment, or the like. In various alternatives, the input control devices 36 may additionally or alternatively include joystick devices, trackballs, data gloves, trigger-guns, hand-operated controllers, voice recognition devices, touch screens, body motion or presence sensors, and the like. In some embodiments and for some associated medical tools 14, the input control devices 36 will provide the same degrees of freedom as their associated medical tools 14 to provide the operator S with telepresence, or the perception that the input control devices 36 are integral with the tools 14 so that the operator S has a sense of directly controlling the tools 14. In other embodiments, the input control devices 36 may have more or fewer degrees of freedom than the associated medical tools and still provide the operator S with telepresence. To this end, position, force, and tactile feedback sensors (not shown) may be employed to transmit position, force, and tactile sensations from the tools 14 back to the operator S's hands through the input control devices 36. An operator input system 16 of the operator's console 38 may also include input control devices 37, which are foot pedals that receive input from a user's foot.

In some embodiments, the operator input system 16 includes sensor systems 40 located on input control devices 36 and 37. The sensor systems 40 may include one or more sensors including, for example, an inertial measurement unit (IMU), an electromagnetic sensor, a shape sensor, a hybrid sensor system incorporating two or more sensing technologies, other suitable sensor systems, and a combination thereof. An example shape sensor is an optical fiber sensor such as a fiber sensor using Fiber Bragg Grating (FBG) or Raleigh scattering technology. In some examples, the IMU may include an accelerometer configured to measure the linear acceleration of the input control devices 36 and 37, and a gyroscope configured to measure the angular velocity of the input control devices 36 and 37. The sensor systems 40 may provide input control device measurement data (e.g., pose data, acceleration data, and angular velocity data of input control devices 36 and 37) of various state estimates such as position, velocity, and acceleration estimates to the control system 20. In some embodiments, the sensor system 40 is located on an end effector of the input control devices 36 or 37 and provides data for a full 6-DOF acceleration commanded by an operator.

As discussed above, flexibility in a manipulator assembly may cause under-damped vibrations and long settling times. In a system where the manipulator assembly has a relatively large flexibility and/or with relatively large masses and inertias, motions commanded by the operator using an operator input system may cause such vibrations. While performing a medical or non-medical procedure, such vibrations experienced on the manipulator or a tool supported by the manipulator may cause control problems. For example, such vibrations may make it difficult for the computer-assisted system to achieve or follow commanded trajectories. Such vibrations may negatively affect control in all types of robotic systems, including for example, industrial and medical robotic systems. In a medical robotic example, such vibrations may make it difficult for a medical robotic system to perform the commanded manipulations of tissue, movement of imaging systems such as endoscopes and ultrasonic probes, insertion of needles, application of sutures, etc. For a further example, in some embodiments where the manipulator or a tool supported by the manipulator moves about a remote center of motion, the vibrations may cause the manipulator or the tool to move as if the remote center itself has moved from its original or modeled position beyond a predetermined tolerance. As discussed in detail below, by using link sensor systems of the manipulator assembly to provide link data, a master/slave system may control the robotic manipulator assembly such that those vibrations are reduced (e.g. smaller vibration amplitudes, faster settling times, etc.).

Figure 2A:
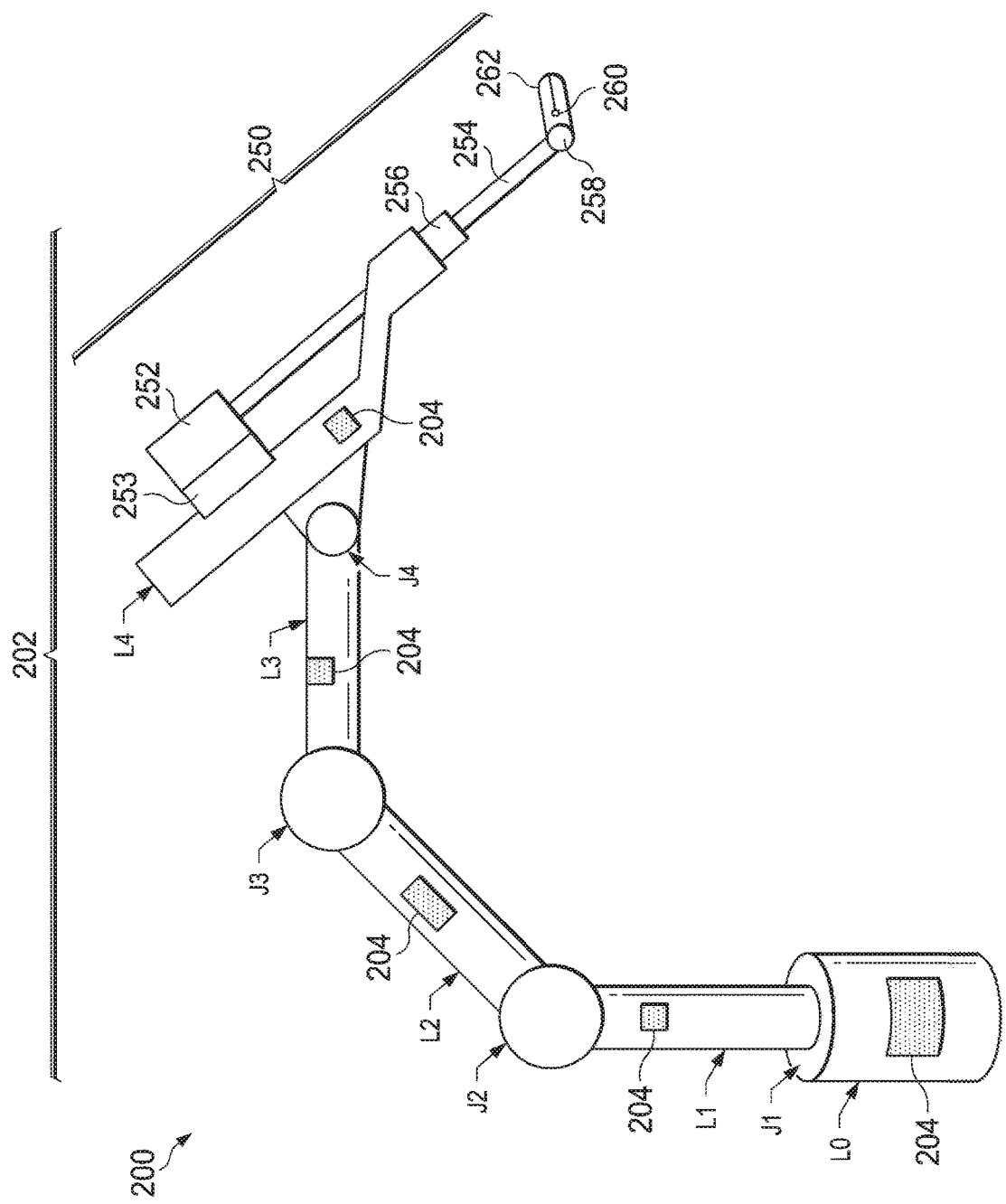
FIGS. 2A and 2B illustrate various embodiments of a robotic manipulator assembly with link sensor systems, in accordance with the present disclosure.
Figure 2B:
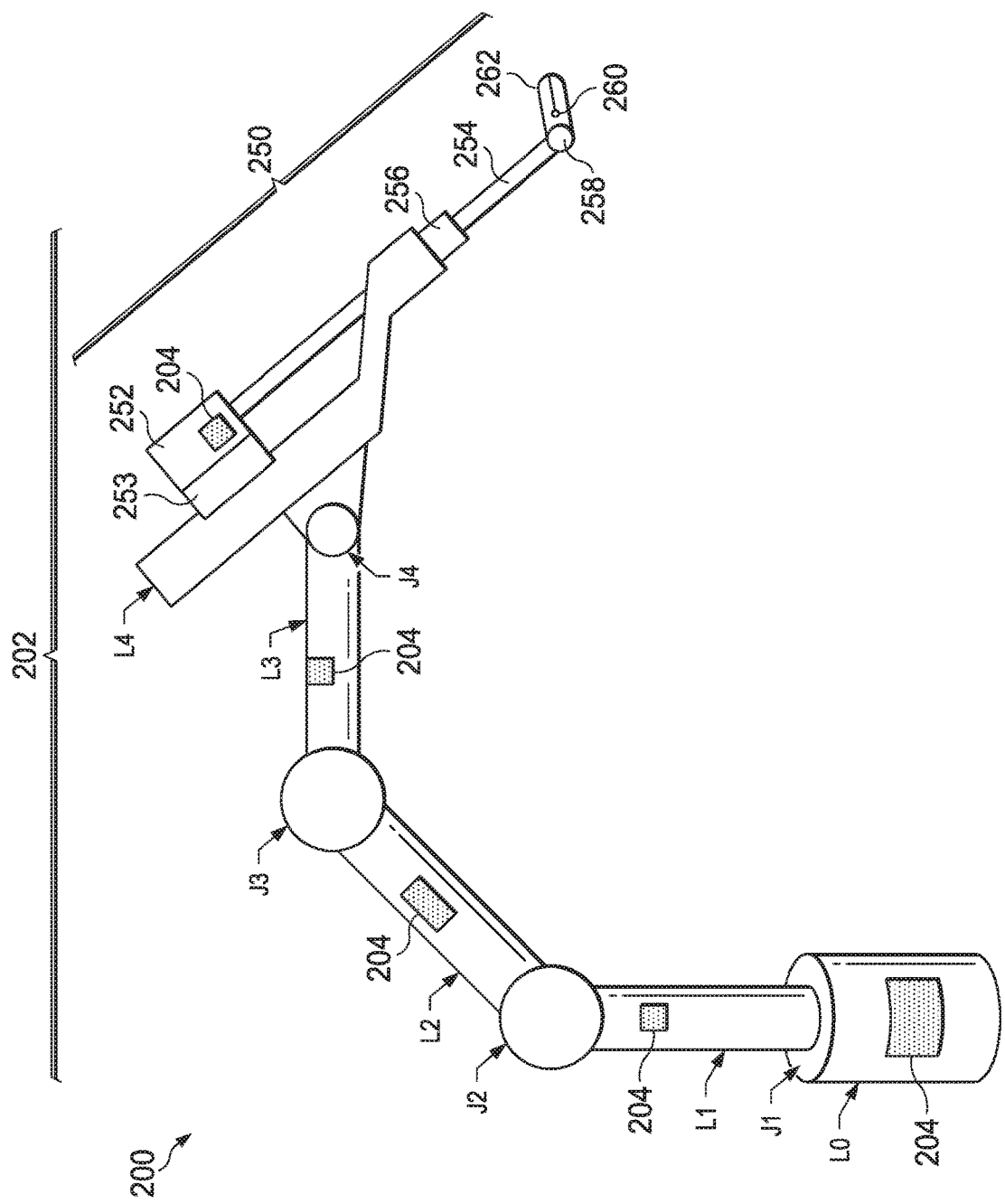

Referring to FIGS. 2A and 2B, in various embodiments, link sensor systems may be attached to links of a manipulator and/or attached to a tool supported by the manipulator. Such link sensor systems may provide to the control system (e.g. the control system 20 for the example of FIGS. 1A-1C) link data, including, for example, measurements and/or estimates of the state (e.g., pose, velocity, acceleration) of the links. The control system may use the link data to control the robotic manipulator assembly to reduce the vibration amplitude and settling time of the tool and remote center movement.

Referring now to FIG. 2A, a manipulator assembly 200 is illustrated. The manipulator assembly 200 may be configured in the form of a patient side cart (e.g., a manipulator assembly 12 for the example of FIG. 1B), or be mounted to a patient side table, to a ceiling mount, to a wall mount, or to a floor mount. In various embodiments, a stand-alone manipulator 202 may be configured in the form of a patient side cart, or be mounted to a patient side table, to a ceiling mount, to a wall mount, or to a floor mount. In the example of FIG. 2A, the manipulator assembly 200 includes a manipulator 202 with an interchangeable tool 250 mounted thereon. The manipulator 202 may be referred herein as a slave manipulator 202, and the tool 250 may be referred herein as a slave tool or instrument 250.

In some embodiments, the tool 250 may be configured for manipulating industrial work pieces, or to manipulate human or animal tissue for reasons other than medical treatment or diagnosis. In some embodiments, the tool 250 may comprise a tool for performing medical procedures. The tool 250 includes a mounting portion 252 and a shaft 254. In the example shown in FIGS. 2A-2B, the mounting portion 252 comprises a mount located on a proximal portion of the tool 250. The mount is configured for removably coupling the tool 250 to a carriage 253 of the manipulator 202. The shaft 254 is coupled to an end effector 260 using a wrist 258. The end effector 260 has a tool tip 262. In some embodiments, the manipulator assembly 200 may include a support for a port device (e.g. a cannula for some medical procedures) that guides or limits movement of the tool 250 relative to the manipulator assembly 200. The tool 250 associated with each manipulator assembly 200 may also be controlled by the operator at an operator input system (e.g. the operator input system 16 for the example of FIGS. 1A-1C).

In more detail, the example manipulator 202 includes links L1, L2, L3, and L4 connected by joints J1, J2, J3, and J4 into a kinematic chain. The tool 250's mounting portion 252 is mounted to a carriage 253 located on link L4. Each of the joints J1, J2, J3, and J4 are controlled by motors. The manipulator 202 may also include an insertion assembly that moves the carriage 253 along L4 and provides insertion and withdrawal motion to the tool 250. Other manipulator designs may not have a moveable carriage 253 or may couple with the tool 250 in another manner, and insert and withdraw the tool 250 by moving one or more joints (e.g. joints J2-J4). Accordingly, at least parts of the manipulator assembly 200 are configured to move using motorized or active joints. In this embodiment, the motors of the manipulator 202 are under the control of the control system (e.g., the control system 20) and may be operated in coordination with motors of other manipulator(s) of the same manipulator assembly 200 if the manipulator assembly 200 has other manipulator(s), or in coordination with other manipulator assemblies, to take desired poses that may assist with advancing over a work piece (or a patient in a medical procedure), mounting of tools, preparation steps, storage, moving to target anatomy inside a patient's body and manipulating tissue, placing the remote center of motion, making space for assistants, obstacles, or equipment around the patient, applying forces to anatomical structures such as for palpating tissue, among other activities. In addition, encoders and other sensors associated with each motor or joint of the manipulator assembly 200 provide feedback to the control system so that the control system receives data about, senses or detects, or determines the motion state of the joint/motor, status, torques applied by or on the joints, and setup of the manipulator assembly 200.

In some embodiments, the manipulator assembly 200 is constrained mechanically or by the use of software, such that it moves the tool 250 about a remote center of motion 256 (also called "remote center 256") during operation. In some embodiments, the remote center of motion 256 is coincident with a shaft of a tool 250 mounted to the manipulator assembly 200. For minimally invasive surgery procedures, typically the position of the remote center of motion 256 is locked at or within the incision in the patient's body wall during at least part of the surgery, during which yaw and pitch motions of the tool 250 about the remote center of motion 256 are allowed to carry out the intended surgical task. Alternatively, the remote center of motion may be located outside of the body to allow a different range of motion. For various procedures, the remote center of motion 256 can be located at any appropriate location for the procedure, such as at a location within a natural orifice or lumen during some medical procedures, a convenient location proximate a work piece during non-medical procedures, etc. Motion about a remote center of motion may be constrained by the use of software (e.g., software of a control system 20) or by a physical constraint defined by a mechanical assembly. In some examples, the procedure may require that the remote center of motion is positioned and maintained within a particular tolerance; that is, the range of location of the virtual fulcrum associated with the motion of the manipulator 202 and/or the tool 250 does not exceed a tolerance amount from a defined remote center of motion. The tolerance may vary, such as varying based on the direction of motion, type of tool, patient habitus, surgical procedure type, etc.

Although each of the joints J1, J2, J3, J4, and carriage 253 may be controlled by an individual or a plurality of joint or actuator controller(s), the joint and actuator controllers may be controlled by a common joint control unit of a common control system (e.g., control system 20, a master/slave control system, etc.). Thus, the tool 250, the tip 262 and end effector 260 of the tool 250, and the manipulator 202 may be controlled through user (e.g., Operator S) manipulation of its associated control device (e.g., the operator input system for the example of FIGS. 1A-1C).

It is noted that the kinematic configuration of the manipulator assembly 200 illustrated in FIG. 2A is exemplary only and not intended to be limiting beyond what is specifically recited in the claims that follow. It will be understood by those skilled in that art in possession of this disclosure that other configurations may be used, and the manipulator assembly 200 may include different numbers, types (e.g., rotary joints, prismatic joints), and combinations of joints. In one example, the manipulator assembly 200 may include a parallelogram linkage. In another example, the manipulator assembly 200 may include a prismatic joint proximal to a base link L0, and one or more rotational joints distal to the base link L0. In that example, the one or more rotational joints distal to a base link L0 may rotate in a particular plane or in three dimensions. In yet another example, the manipulator assembly 200 may include a single-port platform including a base manipulator carrying a plurality of sub-manipulators. In that example, each of the sub-manipulator may be serially connected to the base manipulator.

In the example of FIG. 2A, a link sensor system 204 is attached to each of the links L1, L2, L3, and L4 of a kinematic chain. In various examples, the link sensor system 204 may be located at any portion of its corresponding link (L1, L2, L3, or L4). The link sensor system 204 may include one or more sensors including, for example, an inertial measurement unit (IMU), an shape sensor such as an optical Fiber Bragg Grating (FBG) shape sensor, an electromagnetic sensor, a torque sensor, an optical tracking system, an image tracking system, a hybrid sensor system, other suitable sensor systems, and a combination thereof. In some examples, the link sensor system 204 may include an accelerometer configured to measure the three dimensional linear acceleration of the corresponding link and a gyroscope configured to measure the three dimensional angular velocity of the corresponding link. In some examples, the link sensor system 204 does not include a magnetometer while, in other examples, the link sensor system 204 may include a magnetometer configured to measure the magnetic bearing of the sensor with regard to the earth's magnetic field locally. In some examples, the magnetometer data may be used to supplement the info provided by the accelerometer and gyroscope. By using the link sensor systems 204, higher-order motion estimates of the joints are provided, which may improve the control system performance.

In various embodiments, the manipulator assembly 200 may have different link sensor system arrangements. In the example of FIG. 2B, the manipulator assembly 200 may include a tool 250 that has a link sensor system 204 attached thereon. Specifically, the link sensor system 204 is located on or in the mounting portion 252 of the tool 250. In that particular example, no link system 204 is attached to link L4 of the manipulator 202. Instead, the tool 250 with an attached link system 204 is mounted on link L4 of the manipulator 202, and the link sensor system 204 on the tool 250 provides measurement data of link L4 to the control system. Where the tool 250 can move relative to the link L4, such as where the carriage 253 is moveable with respect to the link L4, the control system can use a model of the interface between the tool 250 and the link L4 (e.g. of carriage 253 relative to the link L4) to transform the data from the link sensor system 204 on the tool 250 to that for link L4. In an example, the interface between the tool 250 and the link L4 (e.g. of carriage 253 relative to the link L4) may be modeled as a link connecting to the link L4 with a prismatic joint. As such, the link sensor system 204 on the tool 250 may also be used as a link sensor system 204 for link L4.

Note that while in FIGS. 2A and 2B, a link sensor system 204 is attached to each link (or a tool rigidly mounted to the link) of a manipulator 202, in some embodiments, the manipulator 202 may include links that do not have any link sensor system attached thereon.

As shown in the example of FIG. 2A, different tools 250 and/or end effectors 260 may be mounted to the manipulator assembly 200 to perform different functions. In that example, those link sensor systems 204 attached to the manipulator 202 may be used with different tools 250 and/or end effectors 260. On the other hand, in the examples of FIG. 2B, the last link L4 of the manipulator 202 does not have its own link sensor system. Instead, it uses a link sensor system 204 located on the tool 250 to provide measurement data of link L4. In that example, some or all of those tools 250 may have a link sensor system 204 attached thereon. As such, using only link sensor systems 204 attached to various portions (e.g., a base, one or more links) of the manipulator 202 may be more cost effective.

As described below with reference to FIGS. 3, 4, 5, 6, 7, and 8, a control system (e.g. the control system 20 for the example of FIGS. 1A-1C) may receive the link data provided by the link sensor systems, and generate joint state (e.g., joint pose, joint velocity, joint acceleration) estimates for the manipulator. As such, a higher-order feedback control loop including acceleration feedbacks may be used to control the joints. The higher-order feedback control loop may provide joint acceleration compensations based on the joint acceleration estimates. Compared to a lower-order feedback control loop using position and velocity feedback errors, such a higher-order feedback control loop using an additional and separate acceleration feedback error allows the manipulator assembly to be more responsive to acceleration transients (e.g., caused by link vibrations). To further reduce the vibrations at a given control point (e.g., a tool tip, a remote center, or another point of interest on the kinematic chain), various weighting schemes may be applied to joint state estimates (e.g., based on joint/link inertias, joint/link physical compliances, and joint/link distances to a control point).

As described in detail below, in some embodiments, a manipulator assembly may have links without attached link sensor systems. For example, a manipulator assembly including a manipulator having a first number of links may only use a second number of link sensor systems, where the second number is less than the first number. In those embodiments, models (e.g., kinematic models, dynamic models) of the manipulator assembly (including its joints, links, tool and portions (e.g., carriage, end effector) of the tool) are used to supplement the joint and link data to generate joint state estimates. The performance of such a manipulator assembly may be improved by configuring the locations of the link sensor systems based on the models associated with the joints and links. For example, the link sensor systems may be attached to the links of the manipulator that are more different to model, and the rest of the links of the manipulator may not have any link sensor systems.

Figure 3:
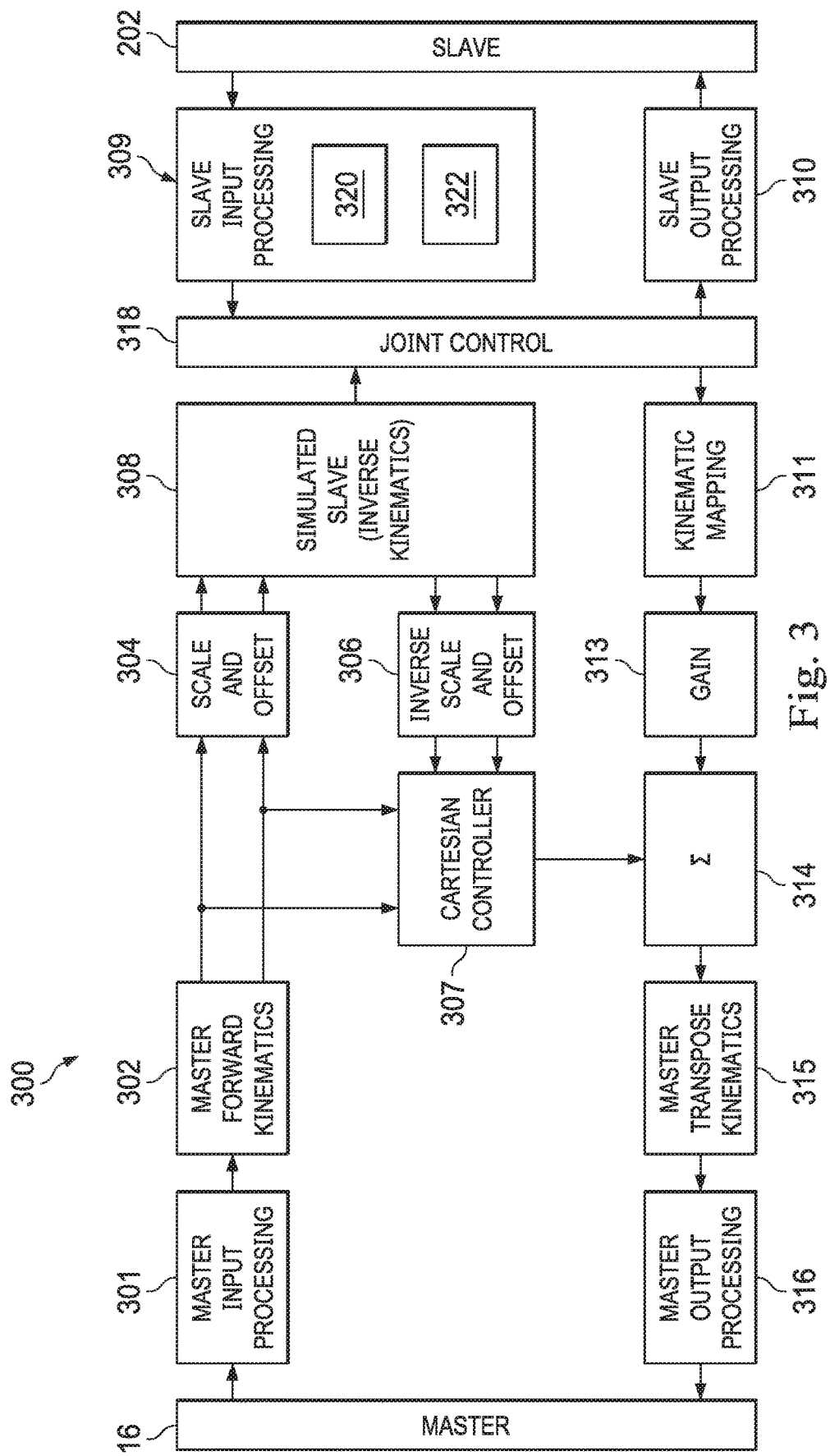
FIG. 3 illustrates a block diagram of a master/slave control system in accordance with an embodiment of the present disclosure.

Referring to FIG. 3, illustrated therein is an example of a control system 300 (e.g., control system 20 for the example of FIGS. 1A-1C). The control system 300 may be used to control the movement of the slave manipulator 202 of the manipulator assembly 200. Consequently, the control system may be used to control the pose and motion of its attached tool 250 and end effector 260, as commanded by movement of an operator (e.g. operator S) or an operator input system (e.g. operator input system 16 for the example of FIGS. 1A-1C). In the description below, the control system 300 is also referred as a master/slave control system 300.

Both the operator input system and slave manipulator may include a number of links connected by joints so as to facilitate multiple degrees-of-freedom movements. As the operator S moves the operator input system from one pose to another during the course of performing a surgical procedure, sensors associated with the operator input system joints provide information indicating such commanded movement in the joint space of the master input device (the "master joint space"). In an example, the commanded movement includes commanded acceleration movement provided by sensors (e.g., sensor systems 40 for the example of FIG. 1C) associated with the operator input system links. Sensors associated with the slave manipulator (e.g., link sensor systems 204 for the examples of FIGS. 2A and 2B associated with the slave manipulator links, joint encoders associated with the slave manipulator joints) provide information indicating slave manipulator movement (and consequently, the tool 250 movement) in slave joint space for feedback purposes. In order to better detect and control fine movements of their respective joints (e.g., in a target velocity range of 0.0005 to 0.01 radians per second at the joint, including the motion during the transition from zero velocity to the velocity in the target range), high-resolution encoders may be used for the joint encoders.

A master input processing unit 301 receives the information of the master joint positions, which are sampled at a control system processing rate, from the master joint encoders in the operator input system, and computes joint velocities from the sensed joint positions. A master forward kinematics processing unit 302 receives the master joint positions and velocities from the master input processing unit 301, and transforms them from master joint space to corresponding positions and velocities of the master frame (i.e., the reference frame associated with the operator input system) in Cartesian space relative to an operator reference frame. In some embodiments, the master forward kinematics processing unit 302 accomplishes this transformation by using a Jacobian and reference frame related information. Example operator reference frames that may be used include the eye reference frame (i.e., the reference frame associated with the position of the operator's eyes). In an embodiment, measurement of Cartesian acceleration may be additionally available from sensor system 40.

A scale and offset processing unit 304 receives the Cartesian pose, velocity, and acceleration commands from the master forward kinematics processing unit 302, scales the commanded movement according to a scale factor selected to perform the procedure, and takes into account offsets to generate desired slave tool frame (i.e., the frame associated with the tool 250) pose and velocities. The scale adjustment is useful where small movements of the slave manipulator 202 of the manipulator assembly 200 are desired relative to the larger movement of the operator input system 16 in order to allow more precise movement of the tool 250 at the procedure site. The offsets, on the other hand, determine, for example, the corresponding position and/or orientation of an end effector frame (e.g., the reference frame associated with an end effector 260 at the distal end of the tool 250) in the camera reference frame (i.e., the reference frame associated with the distal tip of the endoscope) relative to a position and orientation of the master frame in the eye reference frame.

A simulated slave processing unit 308 receives desired slave tool frame position and velocity commands from the scale and offset processing unit 304, and limits the desired slave tool frame state (e.g., pose, velocities, and accelerations) to assigned Cartesian limits for instance to enforce correct and intuitive operation of the tool 250 by keeping it within its dexterous workspace. The simulated slave processing unit 308 generates simulated slave joint states (e.g., positions, velocities, accelerations) corresponding to the limited slave tool frame state, while making sure that the generated slave joint states do not exceed the actual slave joint's range of motion (e.g., velocities and accelerations) and maximum positions even in the vicinity of kinematic singularities for the slave kinematics. In an example, the simulated slave joint states are determined based on a manipulator Jacobian according to the following equations:

$$\dot{q}=J^{-1}\dot{x};\qquad(i)$$

$$\ddot{q}=J^{-1}(\ddot{x}-\dot{J}\dot{q});\qquad(ii)$$

where $\dot{x}$ is the slave tool velocity, $\ddot{x}$ is the slave tool acceleration, J is the Jacobian of the manipulator assembly, $\dot{q}$ is the slave joint velocity, and $\ddot{q}$ is the salve joint acceleration.

An inverse scale and offset processing unit 306 receives the simulated joint position and velocity commands from the simulated slave processing unit 308, and performs an inverse function (inverse to that of the scale and offset processing unit 304) on them. A Cartesian controller 307 receives the inputs to the scale and offset processing unit 304 as first inputs, and the outputs of the inverse scale and offset processing unit 306 as second inputs. The Cartesian controller 307 then generates an error signal as a difference between the first and second inputs, and a Cartesian force "$F_{CART}$" from the error signal such as with the following formula:

$$F_{CART}=K(\Delta x)+B(\Delta\dot{x})+M(\Delta\ddot{x})\qquad(1)$$

where "K" is a spring constant, "B" is a damping constant, M is a mass constant, "$\Delta\dot{X}$" is the difference between the Cartesian velocity inputs to the Cartesian controller 307, "$\Delta x$" is the difference between the Cartesian position inputs to the Cartesian controller 307, and "$\Delta\ddot{x}$" is the difference between the Cartesian acceleration inputs to the Cartesian controller 307.

A master transpose kinematics processing unit 315 receives the Cartesian force $F_{CART}$ through a summation node 314, and generates a corresponding torque in joint space using, for example, the Jacobian transpose matrix and kinematic relationships associated with the operator input system. In systems where the operator input system has motor-driven joints for range-of-motion limits or force feedback, a master output processing unit 316 receives the master torque signals from the master transpose kinematics processing unit 315, generates electrical currents corresponding to the master torque signals, and supplies the electrical currents to corresponding master joint motors of the operator input system (e.g. the operator input system 16 of the example of FIGS. 1A-1C). As a result, an operator S operating such a motor-driven operator input system (e.g. the operator input system 16) feels the Cartesian force, $F_{CART}$, whenever the operator S is commanding a state (e.g., pose, velocity, and/or or acceleration) which exceeds system Cartesian or slave joint limits, or would result in a kinematic singularity condition for the slave manipulator 202 of the manipulator assembly 200.

As the master input processing unit 301 is receiving master joint positions from sensors in the operator input system, a slave input processing unit 309 is also receiving slave positions from sensors in the slave manipulator 202 at the control system processing rate. The slave input processing unit 309 includes a motor side input processing unit 320 receiving slave joint measurement data (e.g., slave joint state data including slave joint pose, velocity, and acceleration data) from motor side sensors (e.g., joint encoders), and a load side (e.g., link side) input processing unit 322 receiving slave link data (e.g., position and motion data of the links L1, L2, L3, and L4 for the example of FIGS. 2A and 2B) from load side sensors (e.g., the link sensor system 204 for the example of FIGS. 2A and 2B). A joint control unit 318 receives the slave joint measurement data and the slave link data from the slave input processing unit 309 and the simulated joint commands provided from the simulated slave processing unit 308, and generates slave torque command signals for the slave joint motors and master torque feedback command signals for the master joint motors. It is noted that in some embodiments, the motor side sensors are not sensitive to link-side vibrations. For example, a flexible joint may be modeled as a motor coupled to a flexible transmission through an r:1 reduction gear, where r is a gear ratio. In that example, the transmission may be dynamically simplified as a linear torsional spring linked directly to the load (e.g., a link). As the gear ratio r gets larger, the motor-side sensor becomes less sensitive to link-side vibrations. By using load side sensors (e.g., the link sensor system 204 for the example of FIGS. 2A and 2B) to provide slave link data including link-side vibrations, better control of the manipulator assembly is achieved by mitigating undesirable vibrations (e.g., link-side vibrations).

The slave torque command signals are generated by the joint control unit 318 so as to drive joints of the slave manipulator until feedback errors calculated in the joint control unit 318 zero out. A slave output processing unit 310 receives the slave torque command signals from the joint control unit 318, converts them into appropriate electrical currents, and supplies the electrical currents to the joint motors of the slave manipulator so as to drive the motors accordingly.

In some embodiments, the master torque feedback command signals are generated by the joint control unit 318 which reflect forces being exerted against the tool 250, or against the slave manipulator supporting the tool 250, back to the operator input system (e.g. the operator input system 16) so that they may be felt in some form by the operator S.

In some embodiments, the joint control unit 318 generates the master torque feedback command signals based on the slave joint position and velocity tracking errors. In some embodiments, the joint control unit 318 generates the master torque feedback command signals based on measurement data from both the slave joint encoders and the link sensor system 204, which is described in detail below. A kinematic mapping unit 311 receives the master torque feedback command signals from the joint control unit 318, and generates the corresponding Cartesian force at the tip of the tool 250 relative to the camera frame of the endoscope using the slave kinematic configuration and the previously calculated slave fulcrum (e.g., remote center 256) position information.

A gain 313 adjusts the magnitude of the Cartesian force so as to ensure system stability while providing adequate force sensation to the operator S. The gain adjusted Cartesian force is then passed through the summation node 314, and processed along with the Cartesian force provided by the Cartesian controller 307 through the master transpose kinematics processing unit 315 and master output processing 316 as previously described in reference to their processing of the Cartesian force provided by the Cartesian controller 307.

The joint control unit 318 includes a joint controller for each active joint of the slave manipulator 202 of the manipulator assembly 200 that is being controlled by the master/slave control system 300. In particular, where the slave manipulator 202 includes joints J1, J2, J3, J4, and a carriage 253 moveable along the link L4, such as the slave manipulator 202 for the examples of FIGS. 2A and 2B, each of these joints or actuators may have its own controller, as will each of the drivable mechanical elements for the tool wrist and end effector mechanisms.

Figure 4:
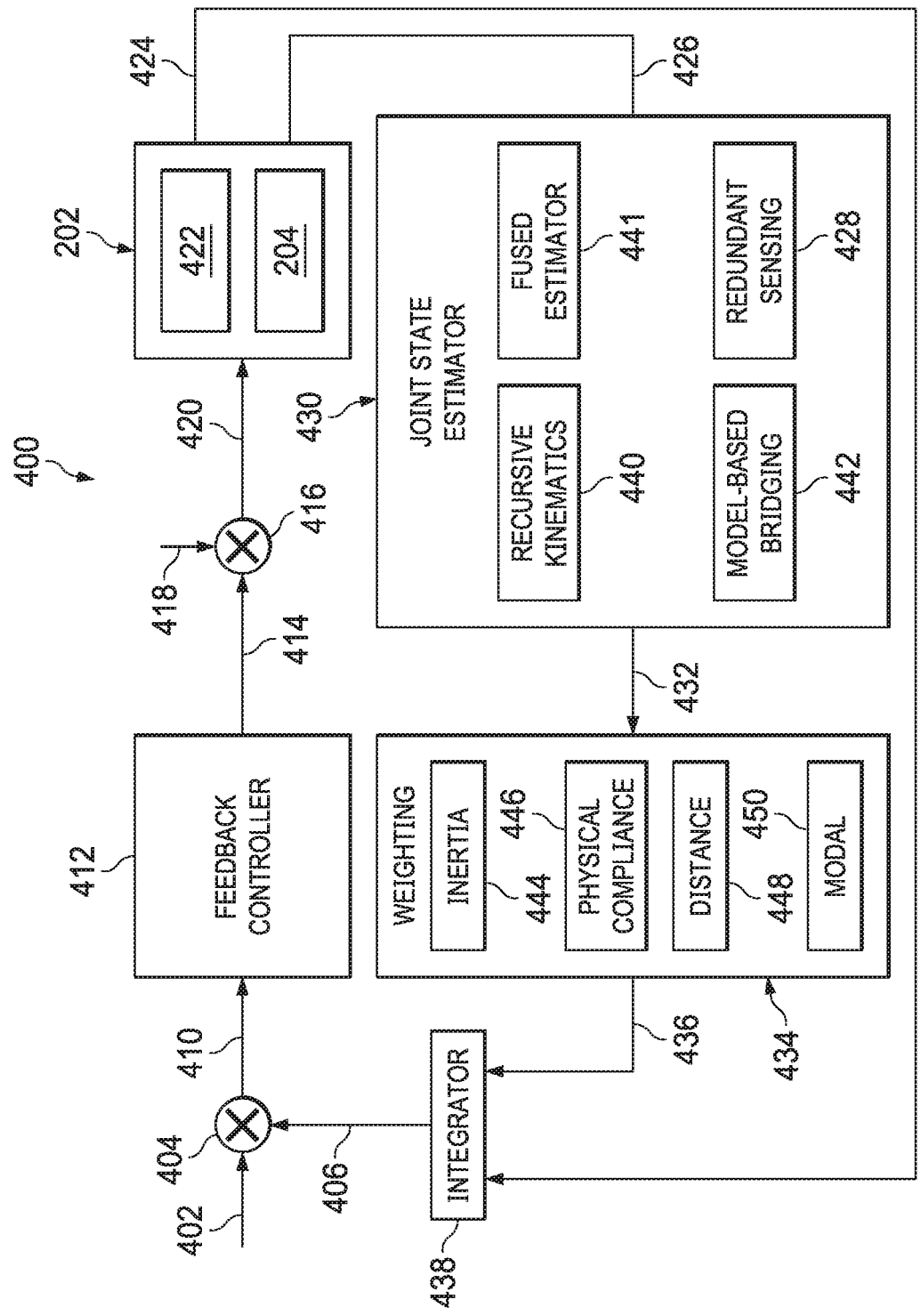
FIG. 4 illustrates a block diagram of a slave joint controller in accordance with an embodiment of the present disclosure.

Referring to FIG. 4, illustrated therein is a joint control unit 400 (e.g., joint control unit 318 of FIG. 3) that uses link data provided by the link sensor systems to feedback a joint acceleration feedback error. In some embodiments, joint measurement data may be used in addition to link sensor data to determine joint acceleration feedback error. Specifically, the joint control unit 400 includes a feedback controller that handles the joint acceleration feedback error caused by acceleration transients caused by link vibrations separately (e.g., by using an acceleration component of the feedback controller). As such, those higher-order (e.g., acceleration) transients may be responded to faster before they are integrated (e.g., computationally and/or mathematically) into lower-order (e.g., position and velocity) feedback errors handled by the feedback controller. This allows the joint controller to be more responsive to acceleration transients caused by link vibrations.

In the example of FIG. 4, the joint control unit 400 includes a comparator 404 that receives desired joint state data 402 denoted as $\Theta_d$ and actual joint state estimates 406, denoted as $\tilde{\Theta}_{act}$. In some embodiments, the desired joint state data 402 $\Theta_d$ is provided by the simulated slave processing unit 308 in response to inputs from the operator input system (e.g. operator input system 16 of FIGS. 1A-1C).

In some embodiments, the desired joint state data 402 $\Theta_d$ may include a desired joint position $\theta_d$, a desired joint velocity $\dot{\theta}_d$, and a desired joint acceleration $\ddot{\theta}_d$. In an example, the desired joint acceleration $\ddot{\theta}_d$ is generated based on operator input acceleration measurement data provided by an acceleration sensor in the operator input system (e.g., sensor 40 operator input system 16 of FIGS. 1A-1C). In another example, the desired joint acceleration $\ddot{\theta}_d$ is provided by a desired joint acceleration estimator, which receives inputs from the operator input system 16, and estimates the desired joint acceleration $\ddot{\theta}_d$ using various state-space filters, which may provide a numerical estimate of acceleration based on desired position and velocity data.

In some embodiments, the actual joint state estimates 406 $\tilde{\Theta}_{act}$ include an actual joint pose estimate $\tilde{\theta}_{act}$, an actual joint velocity estimate $\dot{\tilde{\theta}}_{act}$, and an actual joint acceleration estimate $\ddot{\tilde{\theta}}_{act}$. The comparator 404 compares the desired joint state data 402 $\Theta_d$ and actual joint state estimates 406 $\tilde{\Theta}_{act}$ to generate joint feedback errors 410, denoted as $\Theta_{err}$. The joint feedback errors $\Theta_{err}$ may include a joint position feedback error $\theta_{err}$ including a difference between the desired joint position $\theta_d$ and actual joint pose estimate $\tilde{\theta}_{act}$, a joint velocity feedback error $\dot{\theta}_{err}$ including a difference between the desired joint velocity $\dot{\theta}_d$ and actual joint velocity estimate $\dot{\tilde{\theta}}_{act}$, and a joint acceleration feedback error $\ddot{\theta}_{err}$ including a difference between the desired joint acceleration $\ddot{\theta}_d$ and actual joint acceleration estimate $\ddot{\tilde{\theta}}_{act}$.

The comparator 404 may send join feedback errors 410 $\Theta_{err}$ to a feedback controller 412. The feedback controller 412 may include an acceleration term (denoted as A) for the joint acceleration feedback error of the join feedback errors 410 $\Theta_{err}$. In an example, the feedback controller 412 includes a proportional-derivative-acceleration (PDA) controller. In another example, the feedback controller 412 includes a proportional-integral-derivative-acceleration (PIDA) controller having a closed loop transfer function in the Laplace domain as follows:

$$L(s) = K_a s^2 + K_d s + \frac{K_i}{s} + K_p, \qquad (2)$$

where $K_a$ is the acceleration gain, $K_d$ is the derivative gain, $K_i$ is the integral gain, $K_p$ is the proportional gain, and s is the complex frequency. $K_a$, $K_d$, $K_i$, and $K_p$ are tunable controller parameters, and may be tuned and configured together. By using an acceleration error term, such as a term generated using joint state estimate and the acceleration signal in an appropriate frame from sensor system 40, the performance (e.g., controlled damping, settling time, tracking error) of the feedback controller 412 is improved. In an example, in response to a step disturbance (e.g., a step disturbance detected and transmitted to the controller, such as due to a physical tap on one or more links of the manipulator 202 while the manipulator 202 is moving to a pre-defined pose, there is about 50% reduction in setting time and increased controlled damping behavior compared to a feedback controller without an acceleration term.

In some embodiments, the feedback controller 412 may be designed by interpreting $K_a$ as electronic inertia. In such embodiments, the PDA form of feedback controller 412 is considered to result in a closed loop transfer function (CLTF(s)) for a simple spring mass damper system as follows:

$$CLTF(s) = K_a s^2 + K_d s + K_p / [(m+K_a)s^2 + (b+K_d)s + (k+K_p)], \qquad (3)$$

where $K_a$ is the acceleration gain, $K_d$ is the derivative gain, $K_p$ is the proportional gain, s is the complex frequency, m, b, k are the manipulator joint's natural (or open-loop) parameters for mass, damping, and stiffness respectively. In an example, $K_a$ is determined based on apparent mass $(m+K_a)$, $K_d$ is determined based on closed loop damping $(b+K_d)$, and $K_p$ is determined based on servo stiffness $(k+K_p)$. As such, the closed loop performance of the feedback controller 412 may be specified in terms of a bandwidth determined by the apparent mass and servo stiffness, together with closed loop damping ratio (determined by closed loop damping).

As illustrated in FIG. 4, the feedback controller 412 receives joint feedback errors 410 $\Theta_{err}$ including a joint acceleration feedback error $\ddot{\theta}err$, and generates a slave torque command signal 414. The slave torque command signal 414 is assumed to go through a combiner 416, which represents adjustments to the slave torque command signal 414 based on a disturbance torque 418 (also called "disturbances" in this disclosure) to generate an adjusted slave torque command signal 420. Torque disturbance 418 abstracts unmodeled effects in the joint. The adjusted slave torque command signal 420 may be sent to the slave manipulator system 200, and be used to drive motors (e.g., motors for joints J1, J2, J3, J4) of the slave manipulator 202.

In some embodiments, the slave manipulator 202 includes joint encoders 422 providing joint encoder data 424 (denoted as $\Theta_{enc}$) of the joints J1, J2, J3, and J4 of FIGS. 2A-2B. The joint encoder data 424 $\Theta_{enc}$ may include joint position data $\theta_{enc}$ and joint velocity estimate data $\dot{\Theta}_{enc}$. In some examples, the joint encoder data 424 $\Theta_{enc}$ do not include joint acceleration data. The slave manipulator 202 also includes link sensor systems 204 providing link measurement data 426. The link measurement data 426 may include linear acceleration data $\ddot{x}$ and angular velocity data $\omega$ of the links (e.g., links L1, L2, L3, and L4 of FIGS. 2A-2B). As such, the link measurement data 426 for a particular link $L_i$ may be denoted as $$\begin{bmatrix} \ddot{x} \\ \omega \end{bmatrix}.$$

In some embodiments, a joint state estimator 430 receives the joint encoder data 424 $\Theta_{enc}$ and link measurement data 426

$$\begin{bmatrix} \ddot{x} \\ \omega \end{bmatrix}.$$

and generates joint state estimates 432. As discussed in detail below, the joint state estimator 430 may apply different joint state estimation processes based on various link sensor system arrangements (e.g., whether each of the adjacent links has a link sensor system, whether a single link has more than one link sensor systems) and joint state estimation settings (e.g., whether to provide a fused joint state estimate). The joint state estimator 430 may include various estimation blocks, including for example, a recursive kinematics estimator 440, a fused estimator 441, a model-based bridging estimator 442 (also referred to as a bridging estimator 442), a redundant sensing estimator 428, and any other suitable estimation blocks for performing joint state estimation. Specifically, the recursive kinematics estimator 440 uses a kinematic model to generate joint state estimates 432 using the link data. The bridging estimator 442 uses models (e.g., a dynamic model) of the manipulator joints and links to supplement the link data in generating the joint state estimates 432, for example, when a link sensor system 204 is not present on at least one link adjacent to the joint.

Figure 5A:
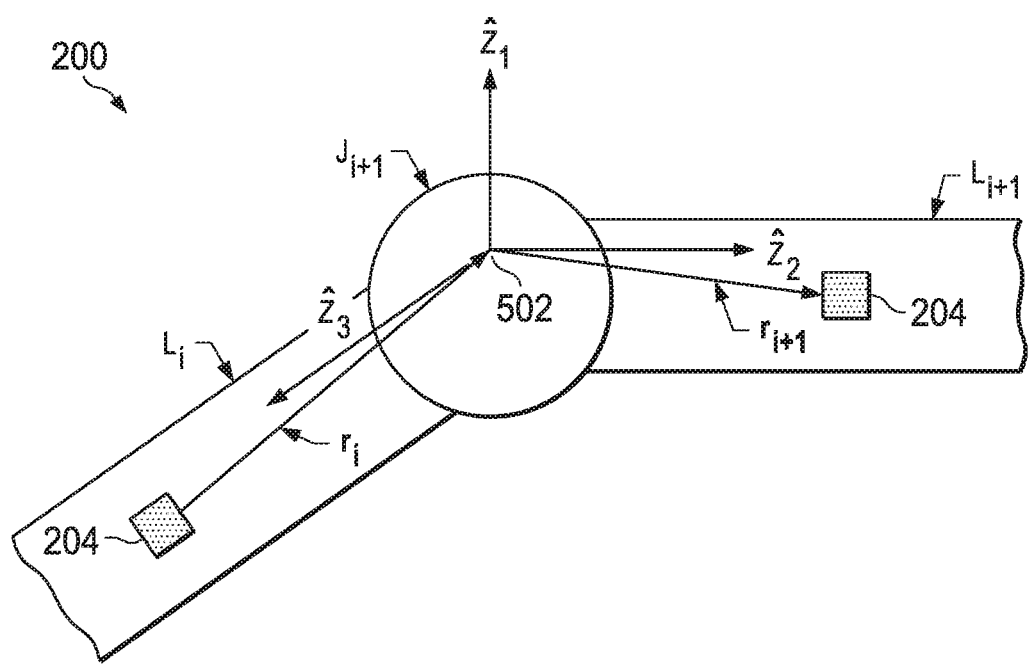
FIG. 5A illustrates a portion of a robotic manipulator assembly with link sensor systems in accordance with an embodiment of the present disclosure.
Figure 5B:
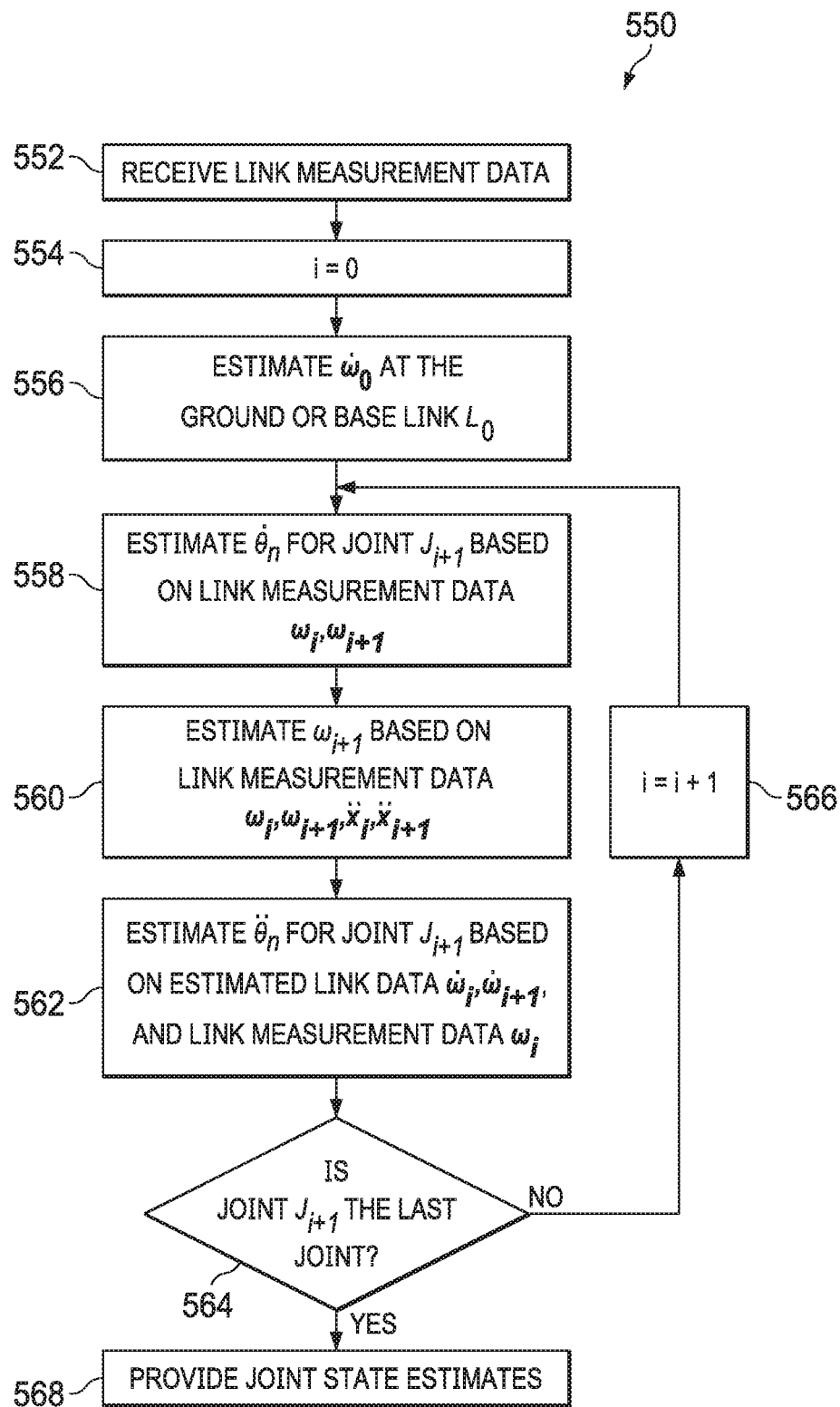
FIG. 5B illustrates a flowchart providing a method for joint state estimation according to an embodiment of the present disclosure.

Referring to FIGS. 5A and 5B, in some embodiments, each link of the manipulator assembly 200 includes a link sensor system 204. In such embodiments, a recursive kinematics estimator 440 of the joint state estimator 430 may generate joint state estimates 432 for all the joints of the manipulator assembly 200 based on recursive kinematics without using a dynamic model of the manipulator links and joints.

Referring to FIG. 5A, illustrated is a portion of a manipulator 202 including adjacent links $L_i$ and $L_{i+1}$ coupled to a joint $J_{i+1}$. Each of the adjacent links $L_i$ and $L_{i+1}$ has a link sensor system 204. The joint $J_{i+1}$ may include joint axes with known direction cosines in a reference frame W (also referred to as the world reference frame) in which link sensor system measurements are made. In an example, the joint axes are mutually perpendicular. While a single joint $J_{i+1}$ is used as an example in the descriptions, in various embodiments, the two adjacent links may be connected to a joint complex including one or more joints. In the particular example of FIG. 5A, the joint $J_{i+1}$ is a spherical wrist defined by a kinematic triad with three mutually perpendicular joint axes $\hat{Z}_1$, $\hat{Z}_2$, $\hat{Z}_3$. While in some embodiments the joint $J_{i+1}$ allows three degrees of freedom, in other embodiments, a joint $J_{i+1}$ with one degree of freedom (DOF) or two degrees of freedom (e.g., a rotary dyad with two mutually perpendicular axes $Z_1$ and $Z_2$) may be used.

In an example, the recursive kinematics estimator 440 may perform the joint state (e.g., velocity and acceleration) estimation based on a kinematic model using the Denavit and Hartenberg (DH) convention. The DH convention uses kinematic parameters (also referred to as DH parameters) including joint angle $\theta_i$, link offset $d_i$, link length $a_i$, and link twist $\alpha_i$ corresponding to one degree of freedom. These kinematic parameters may be used to describe the translation and rotation between two adjacent links $L_i$ and $L_{i+1}$ coupled at a 1-DOF joint $J_{i+1}$. In some embodiments, because the recursive kinematics estimator 440 relies on the incremental differential kinematics between two adjacent links, the kinematic parameters in the kinematics model defining these differential kinematics are calibrated to ensure the accuracy of the recursive kinematics estimator 440.

The kinematics between two adjacent links $L_i$ and $L_{i+1}$ may be represented by the following equations:

$$\omega_{i+1} = \omega_i + \Sigma_n \lambda_n (R_{DH_n}{}^W \dot{\theta}_n \hat{Z}_n), \tag{4}$$

$$\dot{\omega}_{i+1} = \dot{\omega}_i + \Sigma_n \lambda_n (R_{DH_n}{}^W \ddot{\theta}_n \hat{Z}_n + \omega_i \times \dot{\theta}_n Z_n), \tag{5}$$

$$\dot{x}_{i+1} = \dot{x}_i + \omega_i \times r_i + \omega_{i+1} \times r_{i+1} + \Sigma_n (1-\lambda_n)(R_{DH_n}{}^W \dot{\theta}_n \hat{Z}_n), \tag{6}$$

$$\ddot{x}_{i+1} = \ddot{x}_i + \dot{\omega}_i \times r_i + \omega_i \times \omega_i \times r_i + \dot{\omega}_{i+1} \times r_{i+1} + \omega_{i+1} \times \omega_{i+1} \times r_{i+1} + \Sigma_n (1-\lambda_n)(R_{DH_n}{}^W \ddot{\theta}_n \hat{Z}_n + 2\omega_{i+1} \times \dot{\theta}_n Z_n). \tag{7}$$

In those equations, × represents the vector cross product operator, n is the joint axis index (e.g., 1, 2, 3) belonging to the joint $J_{i+1}$. $\hat{Z}_n$ is the $n^{th}$ joint axis. $\dot{\theta}_n$ is the joint velocity associated with (e.g., projected on) the $n^{th}$ joint axis. $\ddot{\theta}_n$ is the joint acceleration associated with (e.g., projected on) the $n^{th}$ joint axis. $R_{DH_n}{}^W$ is a rotation matrix transforming vectors in the joint's (e.g., the $n^{th}$ joint axis) DH frame to the reference frame W in which link sensor system 204 measurements are made. $\lambda_n$ is a constant indicating whether the motion along the $n^{th}$ joint axis is rotary (e.g., $\lambda_n=1$) or prismatic (e.g., $\lambda_n=0$). $\omega_i$ and $\omega_{i+1}$ are link angular velocities provided by link data of link sensor systems 204 on adjacent links $L_i$ and $L_{i+1}$ respectively. $\ddot{x}_i$ and $\ddot{x}_{i+1}$ are link translational acceleration provided by link data of link sensor systems 204 on adjacent links $L_i$ and $L_{i+1}$ respectively. $r_i$ is a vector from the link sensor system 204 on link $L_i$ to an origin 502 where joint axes of the joint $J_{i+1}$ intersect. $r_{i+1}$ is a vector from origin 502 to the link sensor system 204 on link $L_{i+1}$.

Based on equations (4) through (7), the recursive kinematics estimator 440 may perform joint state estimation based on recursive kinematics. Referring to FIG. 5B, illustrated is a method 550 for joint state estimation based on recursive kinematics as a set of operations 552 through 568 (also called processes 552 to 568). Not all of the illustrated operations 552 through 568 may be performed in all embodiments of method 550. Additionally, one or more processes that are not expressly illustrated in FIG. 5B may be included before, after, in between, or as part of the operations 552 through 568. In some embodiments, one or more of the processes may be implemented, at least in part, in the form of executable code stored on non-transitory, tangible, machine-readable media that when run by one or more processors (e.g., the processors of control system) may cause the one or more processors to perform one or more of the processes. While the examples below use joints having rotary axes where $\lambda_n$ equals 1, they be similarly extended to joints having prismatic axes or a combination of rotary and prismatic axes.

The method 550 begins at operation 552, where the recursive kinematics estimator 440 receives link measurement data 426 from link sensor systems 204 located on links of a manipulator 202. The link measurement data 426 may include link angular velocity data or link acceleration data. The method 550 may proceed to operation 554 to set iteration index i to zero. The method 550 may then proceed to operation 556, where $\omega_0$ is estimated at the ground or base link $L_0$. In an example, the recursive kinematics estimator 440 may set $\omega_0$ to have a value zero. In such an example, the link $L_0$ may be a link in the chain which does not move dynamically (e.g., a link configured to be moved slowly, or set in a position, locked, and not moved again during a particular operation). Such a link $L_0$ may be a setup structure or setup joints of the manipulator assembly or a vertical column at a base of the manipulator assembly. In another example where a base link $L_0$ has redundant (more than one) sensors, $\omega_0$ may be computed. Such computation may include numerically differentiating the measurement data of the redundant sensors and incorporating a filter (e.g., a Kalman filter).

The method 550 may then proceed to operation 558 to estimate the joint velocity $\dot{\theta}_n$ for joint $J_{i+1}$ based on link measurement data $\omega_i$ provided by the link sensor system 204 on the link $L_i$ and link measurement data $\omega_{i+1}$ provided by the link sensor system 204 on the link $L_{i+1}$. In an example, at operation 558, the recursive kinematics estimator 440 may estimate the joint velocity $\dot{\theta}_n$ according to equation (4) as follows:

$$\dot{\theta}_n = (\omega_{i+1} - \omega_i) \cdot (R_{DH_n}{}^W \hat{Z}_n) = \Delta\omega \cdot (R_{DH_n}{}^W \hat{Z}_n) \quad (8)$$

As shown in equation (8), the differential angular velocity $\Delta\omega$ of adjacent links $L_i$ and $L_{i+1}$ may be computed using $\omega_i$ and $\omega_{i+1}$. The joint velocity $\dot{\theta}_n$ for joint $J_{i+1}$ may then be estimated by transforming the differential angular velocity $\Delta\omega$ to the joint space by applying $R_{DH_n}{}^W \hat{Z}_n$. In some embodiments, the difference between the joint velocity estimate $\dot{\theta}_n$ and a joint velocity estimate based on motor or link side encoders may be monitored. For operational safety, in the event of sensor faults and other unexpected conditions, a fault condition could be generated when the said difference in the above redundant velocity estimates is greater than a preconfigured threshold. Such a difference may be monitored for joint position, Cartesian position, or Cartesian velocity. Transformations between joint and Cartesian space velocities may be determined based on equation (i).

The method 550 may then proceed to operation 560, where the recursive kinematics estimator 440 may compute an estimation for angular link acceleration $\dot{\omega}_{i+1}$ for link $L_{i+1}$ based on link measurement data $\omega_i$, $\omega_{i+1}$, $\ddot{x}_i$, $\ddot{x}_{i+1}$ and estimated link data $\dot{\omega}_i$ according to equations (7) as follows:

$$\dot{\omega}_{i+1} = (r_{i+1} \times)^{-1}(-(\ddot{x}_{i+1} - \ddot{x}_i) + \omega_i \times r_i + \omega_i \times \omega_i \times r_i + \omega_{i+1} \times \omega_{i+1} \times r_{i+1}). \quad (9)$$

In the $i^{th}$ iteration where $i=0$, $\dot{\omega}_1$ is computed based the estimated angular link acceleration $\dot{\omega}_0$ generated at operation 556. In the $i^{th}$ iteration where i is greater than 0, $\dot{\omega}_{i+1}$ is computed based the estimated angular link acceleration $\dot{\omega}_i$ generated at operation 560 in the previous $(i-1)^{th}$ iteration.

The method 550 may then proceed to operation 562, where the recursive kinematics estimator 440 computes joint acceleration $\ddot{\theta}_n$ for joint $J_{i+1}$ using estimated link data $\dot{\omega}_i$ and $\dot{\omega}_{i+1}$ and link measurement data $\omega_i$ as follows:

$$\ddot{\theta}_n = (\dot{\omega}_{i+1} - \dot{\omega}_i) \cdot R_{DH_n}{}^W \hat{Z}_n - \Sigma_n([\omega_i \times \dot{\theta}_n \hat{Z}_n] \cdot [R_{DH_n}{}^W \hat{Z}_n]). \quad (10)$$

In some embodiments, the recursive kinematics estimator 440 may perform kinematic estimation for $\dot{x}_{i+1}$ according to equation (6) using $\dot{x}_i$, $\omega_i$, $r_i$, $\omega_{i+1}$, $r_{i+1}$, $R_{DH_n}{}^W$, and $\ddot{\theta}_n$. In an example, the estimate of $\dot{x}_{i+1}$ is used in joint state estimation where the corresponding joint is a prismatic joint.

The method 550 may then proceed to operation 564, where the recursive kinematics estimator 440 determines whether the joint $J_{i+1}$ is the last joint of the manipulator assembly for joint state estimation. In some embodiments, the recursive kinematics estimator 440 determines that the joint $J_{i+1}$ is not the last joint, and the method 550 continues to operation 556 to increase in the iteration index i by one, and then performs the next iteration including operations 558 through 564 to perform joint state estimation for the next joint in the serial chain.

In some embodiments, at operation 564, the recursive kinematics estimator 440 determines that the joint $J_{i+1}$ is the last joint for joint state estimation. The method 550 may then proceed to block 568, where the recursive kinematics estimator 440 outputs the joint state estimates 432.

As discussed above, the joint state estimates 432 (e.g., $\dot{\theta}_n$, $\ddot{\theta}_n$) may be determined based on the link measurement data and the rotation matrix $R_{DH_n}{}^W$. As such, the accuracy of the joint state estimates 432 may be affected by the accuracy of the link measurement data and the rotation matrix $R_{DH_n}{}^W$. Accordingly, in various embodiments, the link sensor systems 204 and/or the rotation matrix $R_{DH_n}{}^W$ may be calibrated to an acceptable tolerance.

Figure 6A:
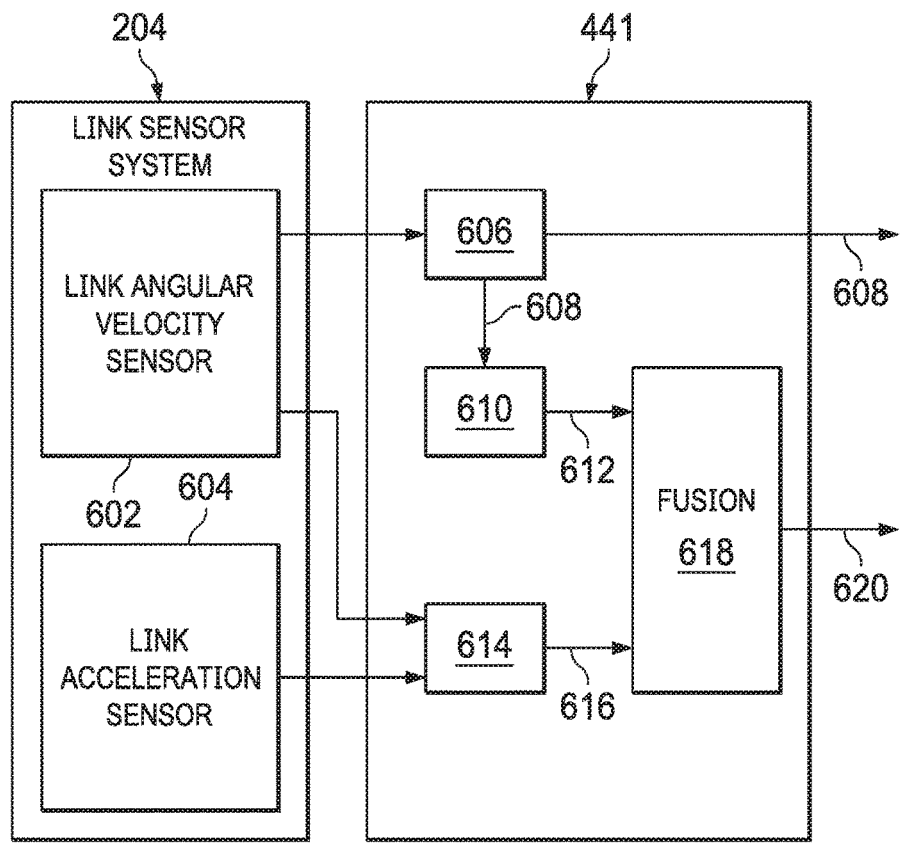
FIG. 6A illustrates a block diagram of a fused estimator in accordance with an embodiment of the present disclosure.

Referring to FIGS. 4 and 6A, in some embodiments, a fused estimator 441 of the joint state estimator 430 (e.g., joint state estimator 430 of FIG. 4) may generate joint acceleration estimates based on robustness requirements and/or link data (e.g., link angular velocity data, link acceleration data) availability. In an example, each link sensor system 204 may include a link angular velocity sensor 602 (e.g. a gyroscope) configured to measure the angular velocity of a link, and/or a link acceleration sensor 604 (e.g., an accelerometer) configured to measure link acceleration. In an example, a first joint acceleration estimate may be generated only based on link angular velocity data $\omega_i$ and $\omega_{i+1}$ without using link acceleration data $\ddot{x}_i$ and $\ddot{x}_{i+1}$. In one example, the first acceleration estimate may be used when the link acceleration sensor 604 is unavailable and the estimate can be determined only based on the measurements of a link angular velocity sensor 602. In another example, a fused joint acceleration estimate may be generated using the first joint acceleration estimate and second joint acceleration estimate computed based link angular velocity data, link acceleration data, manipulator dynamic model, and/or kinematics of the manipulator. Such fusion may improve the robustness and signal-to-noise ratio (SNR) of the joint acceleration estimate.

Referring to the example of FIG. 6A, in some embodiments, the fused estimator 441 includes a joint velocity estimator 606. The joint velocity estimator 606 receives angular velocity data $\omega_i$ and $\omega_{i+1}$ of adjacent links $L_i$ and $L_{i+1}$, computes differential angular velocity $\Delta\omega$ (e.g., according to equation (6)), and generates joint velocity estimate 608 of joint $J_{i+1}$ by transforming the differential angular velocity $\Delta\omega$ to the joint space associated with the joint $J_{i+1}$ (e.g., according to equation (5)).

In some embodiments, a first joint acceleration estimator 610 of the recursive kinematics estimator 440 receives the joint velocity estimates 608 from the joint velocity estimator 606, and generates a first joint acceleration estimate 612 by based on the joint velocity estimates 608. As such, the first joint acceleration estimate 612 is generated only based on link angular velocity data $\omega_i$ and $\omega_{i+1}$ without using link acceleration data $\ddot{x}_i$ and $\ddot{x}_{i+1}$. In some examples, the first joint acceleration estimate 612.

In some embodiments, a fusion joint acceleration estimator 618 of the recursive kinematics estimator 440 receives first joint acceleration estimate 612 from the first joint acceleration estimator 610, and receives second joint acceleration estimate 616 from a second joint acceleration estimator 614. The second joint acceleration estimator 614 may generate joint acceleration estimate 616 using link acceleration data form either adjacent links to the joint or one or more links that are connected to the joint. The fusion joint acceleration estimator 618 may generate a fused joint acceleration estimate 620 by fusing the first joint acceleration estimate 612 and second joint acceleration estimate 616. Because fused joint acceleration estimate 620 is generated based the first joint acceleration estimate 612 and second joint acceleration estimate 616 generated based on different data and/or different estimation models, it may improve the robustness and SNR of the fused estimate.

Figure 6B:
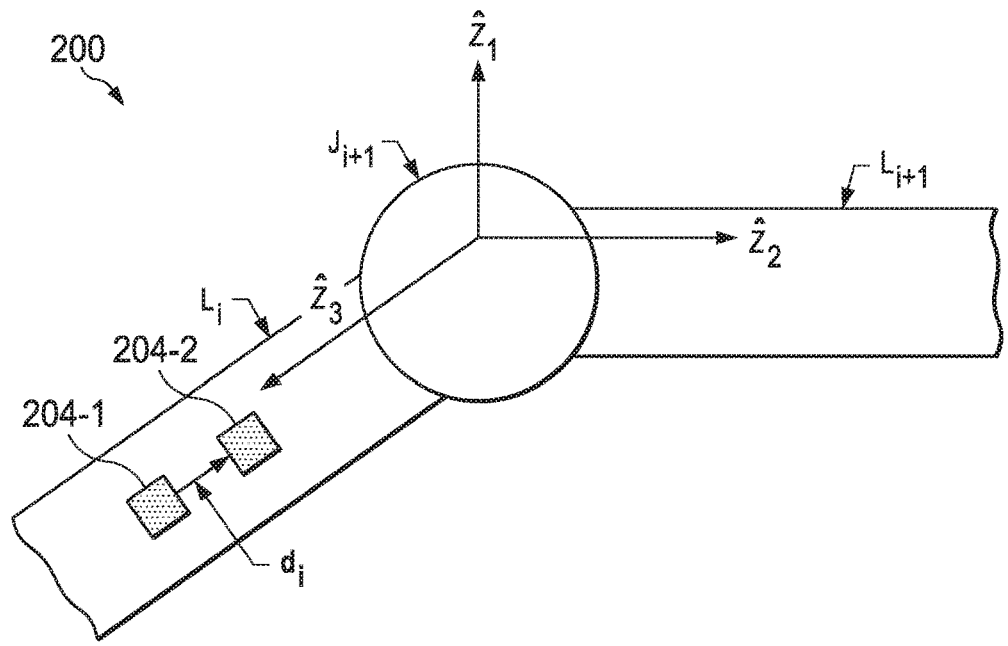
FIG. 6B illustrates a portion of a robotic manipulator assembly with link sensor systems in accordance with an embodiment of the present disclosure.

Referring to FIGS. 4 and 6B, in some embodiments, a redundant sensing estimator 428 of the joint state estimator 430 may generate joint state estimates for a joint based on two or more link sensor systems on a single link (e.g., without using kinematic models). In the example of FIG. 6B, a portion of a manipulator 202 including adjacent links $L_i$ and $L_{i+1}$ coupled to a joint $J_{i+1}$. Link $L_i$ has link sensor systems 204-1 and 204-2, where a vector $d_i$ is a vector from link sensor system 204-1 to link sensor system 204-2, where link sensor system 204-1 is more proximal on the link $L_i$. Because link $L_i$ has more than one link sensor systems, the link sensor systems 204-1 and 204-2 are also referred to as redundant link sensor systems 204-1 and 204-2. As such, link data $\dot{\omega}_i$ may be estimated without using equation (9). Instead, the link data $\dot{\omega}_i$ may be estimated as follows:

$$\dot{\omega}_i = -(d_i \times)^{-1}(\ddot{x}_{link\_sensor\_2} - \ddot{x}_{link\_sensor\_1}),\quad (11)$$

where $\ddot{x}_{link\_sensor\_1}$ and $\ddot{x}_{link\_sensor\_2}$ are the translational acceleration link data from redundant link sensor systems 204-1 and 204-2 respectively, $(\ddot{x}_{link\_sensor\_2} - \ddot{x}_{link\_sensor\_1})$ is the vector difference between translational accelerations of the redundant link sensor systems 204-1 and 204-2. The joint acceleration $\ddot{\theta}_n$ for joint $J_{i+1}$ may then be computed based on equation (10).

Figure 7A:
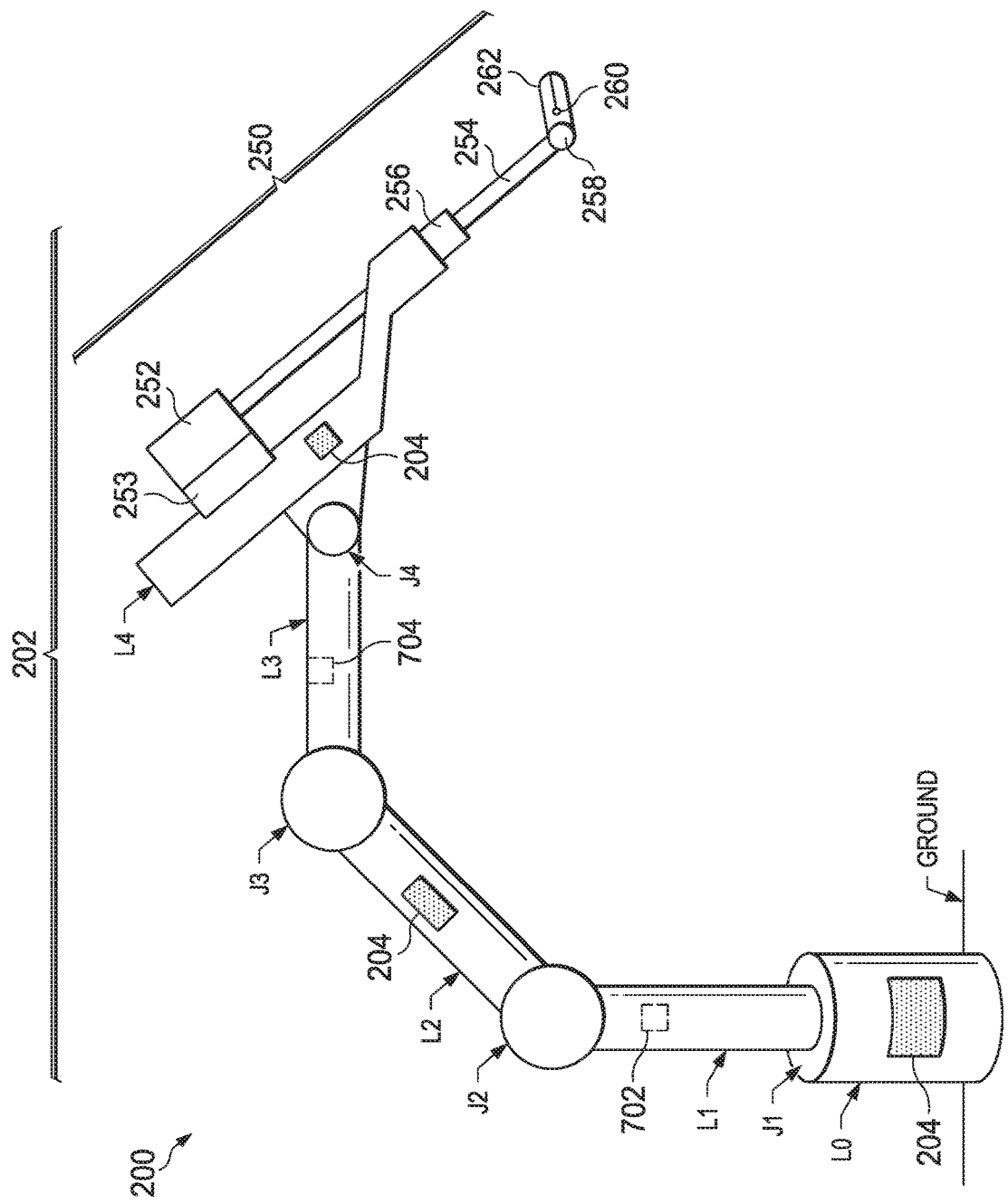
FIG. 7A illustrates a robotic manipulator assembly with link sensor systems in accordance with an embodiment of the present disclosure.
Figure 7B:
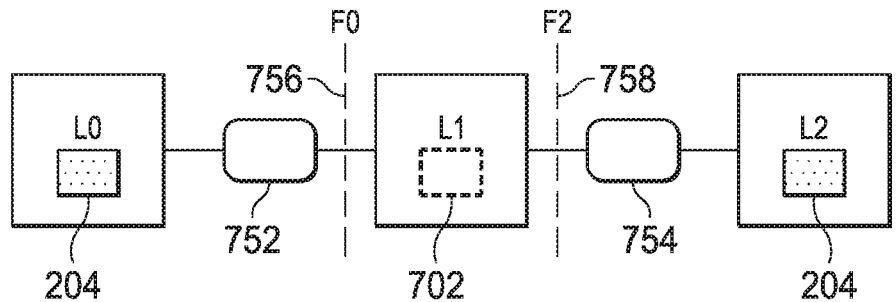
FIG. 7B illustrates joint dynamic models in a portion of a robotic manipulator assembly in accordance with an embodiment of the present disclosure.

Referring to FIGS. 4, 7A, and 7B, in some embodiments, a bridging estimator 442 of the joint state estimator 430 may perform joint state estimation by supplementing the joint encoder data and link measurement data using a model (e.g., a kinematic model, a dynamic model) of the manipulator joints and/or links. Such a model may be used to bridge the gaps of particular links in a manipulator 202 where those particular links do not have link sensor systems attached thereon.

Referring to the example of FIG. 7A, a manipulator 202 includes links L1, L2, L3, and L4 connected by joints J1, J2, J3, and J4 into a kinematic chain. Each of links L2 and L4 includes a link sensor system 204, while there is no link sensor system located on links L1 and L3. The base link L0 may also include a link sensor system 204. In those embodiments, the bridging estimator 442 use models of the manipulator joints, links, and/or tools attached to the manipulator to supplement the joint encoder data and link data.

In some embodiments, the bridging estimator 442 may generate joint state estimates 432 of a particular joint (e.g. joint J2) by fusing intermediate joint state estimates of that particular joint. Each intermediate estimate is generated based on link data from a single link sensor system 204 associated with a particular link. In an example, the particular link (e.g., link L2) is connected to the particular joint J2 and has a link sensor system 204. In another example, the particular link (e.g., link L4) is not connected to the particular joint J2 and has a link sensor system 204. In yet another example, neither of the adjacent links connected to that particular joint has a link sensor system. In that example, all intermediate estimates for that particular joint are generated using link data associated with links not connected to that particular joint.

In some embodiments, the translational acceleration data $\ddot{x}_i$ and angular velocity data $\omega_i$ of a link $L_i$ may be expressed as follows:

$$\ddot{x}_i = J_t \ddot{\theta} + \dot{J}_t \dot{\theta},\quad (12)$$

$$\omega_i = J_\omega \dot{\theta},\quad (13)$$

where $J_t$ is the translational Jacobian of the link sensor system 204 on link $L_i$ in the world reference frame W, $J_\omega$ is the orientational Jacobian of the link sensor system 204 on link $L_i$ in the world reference frame W, $\dot{\theta}$ and $\ddot{\theta}$ are the joint velocities and joint accelerations of joints of the manipulator respectively.

Using equations (11) and (12), the bridging estimator 442 may determine the joint velocity and acceleration estimates of the joints of the manipulator based on link sensor data from a particular link sensor system 204 on a link $L_i$ as follows:

$$\dot{\theta}_{link\_sensor\_i} = J_\omega^{-1}\omega_i,\quad (14)$$

$$\ddot{\theta}_{link\_sensor\_i} = J_t^{-1}(\ddot{x}_i - \dot{J}_t J_\omega^{-1}\omega_i),\quad (15)$$

where $\dot{\theta}_{link\_sensor\_i}$ denotes the estimates for joint velocities of joints of the manipulator based on the link measurement data of link $L_i$, and $\ddot{\theta}_{link\_sensor\_i}$ denotes the estimates for joint accelerations of joints of the manipulator based on the link measurement data of link $L_i$.

Referring to FIG. 7A, in some embodiments, the bridging estimator 442 may generate multiple intermediate joint state estimates using multiple link sensor systems 204 respectively, and generate the joint state estimates by combining the multiple intermediate joint state estimates. In some embodiments, the bridging estimator 442 may apply different weights to the multiple intermediate joint state estimates to generate weighted intermediate joint state estimates, and generate the joint state estimates by combining the multiple weighted intermediate joint state estimates as follows:

$$\dot{\theta} = \Sigma_{i=1}^{M} \text{weight1}_i \dot{\theta}_{link\_sensor\_i}, \quad (16)$$

$$\ddot{\theta} = \Sigma_{i=1}^{M} \text{weight2}_i \ddot{\theta}_{link\_sensor\_i}, \quad (17)$$

where weight1$_i$ is the weight assigned to intermediate estimate $\dot{\theta}_{link\_sensor\_i}$ generated using link data from the link sensor system 204 on link L$_i$, weight2$_i$ is the weight assigned to intermediate estimate $\ddot{\theta}_{link\_sensor\_i}$ generated using link data from the link sensor system 204 on link L$_i$, and M is an integer between 1 and N, N being the total number of available link sensor systems 204. Because the joint state estimates depend on Jacobian J$_t$ and J$_\omega$ determined based on kinematic models of the manipulator, the accuracy of joint state estimates may depend on the accuracy of kinematic calibration of the manipulator.

In the example of FIG. 7A, the bridging estimator 442 may generate the joint state estimate for joint J2 using two intermediate joint state estimates. The first intermediate estimate for joint J2 is generated only using link data from the link sensor system 204 of link L2. The second intermediate estimate for joint J2 is generated only using link data from the link sensor system 204 of link L4.

In some embodiments, the bridging estimator 442 may apply different weights to the first and second intermediate estimates for joint J2. The weights may be based on the distance between the associated link sensor system 204 and a control point (e.g., a tool tip 262). In an example, a weight applied to the second intermediate estimate is greater than the weight applied to the first intermediate estimate, where the second intermediate estimate is associated with the link sensor system 204 of link L4 that is closer to a control point (e.g., a tool tip 262). The weighted first and second intermediate estimates for joint J2 may then be fused to generate the joint state estimate 432 for joint J2.

Note that in the example of FIG. 7A, the bridging estimator 442 may similarly generate joint state estimate for other joints J1, J3, and J4 using intermediate estimates.

Referring to FIGS. 4 and 7A, in some embodiments, the bridging estimator 442 may use a section-by-section scheme for joint state estimation, and compute joint state estimates in sections of a manipulator assembly similarly based on equations 11 through 17 as described above. In such embodiments, for a section of a manipulator assembly includes links L$_{n1-1}$ through link L$_{n2}$ including joints J$_{n1}$ through J$_{n2}$ and the intermediate links thereof, acceleration $\ddot{\theta}(n1:n2)$ of joints J$_{n1}$ through J$_{n2}$ in that section may be computed as follows:

$$\ddot{\theta}(n1:n2) = J_{t\_section}^{-1}(\Delta \ddot{x}_{section} - \dot{J}_{t\_section} J_{\omega\_section}^{-1} \Delta \omega_{section}), \quad (18)$$

where J$_{t\_section}$ is translational Jacobian describing the link sensor system 204 on link L$_{n2}$ with regard to the link sensor system 204 on link L$_{n1-1}$, where J$_{\omega\_section}$ is the orientational Jacobian describing the link sensor system 204 on link L$_{n2}$ with regard to the link sensor system 204 on link L$_{n1-1}$. J$_{t\_section}$ and J$_{\omega\_section}$ may be determined based on kinematic models of the section (e.g., including links L$_{n1-1}$, joints J$_{n1}$ through J$_{n2}$ and the intermediate links thereof, and link L$_{n2}$) of the manipulator, as such, their accuracy depend on the accuracy of kinematic calibration of the manipulator. $\Delta \ddot{x}_{section}$ is the differential translational acceleration of the link sensor system 204 on link L$_{n2}$ with regard to the link sensor system 204 on link L$_{n1-1}$, and may be computed using $\ddot{x}_{n2}$ and $\ddot{x}_{n1-1}$ of the link data from the link sensor systems 204 on links L$_{n2}$ and L$_{n1-1}$. $\Delta \omega_{section}$ is the differential angular velocity of the link sensor system 204 on link L$_{n2}$ with regard to the link sensor system 204 on link L$_{n1-1}$, and may be computed using $\omega_{n2}$ and to $\omega_{n1-1}$ of the link data from the link sensor systems 204 on links L$_{n2}$ and L$_{n1-1}$.

In the example of FIG. 7A, the bridging estimator 442 may use a section-by-section scheme by using a first section includes J$_1$ and J$_2$ bracketed by the link sensor systems on L$_0$ and L$_2$, and a second section includes J$_3$ and J$_4$ bracketed by the link sensor systems on L$_2$ and L$_4$. The joint acceleration $\ddot{\theta}(1:2)$ of the first section may be determined based on the Jacobian of the link sensor system 204 of link L2 located at the last link (L2) of the first section with regard to ground or base link L0. The joint acceleration $\ddot{\theta}(3:4)$ of the second section may be determined based on the Jacobian of the link sensor system 204 of link L4 located at the last link (L4) of the second section with regard to the link sensor system 204 located at link L2.

Referring to FIGS. 4, 7A, and 7B, in some embodiments, the model-based bridging estimator 442 of the joint state estimator 430 may use dynamic models associated with the manipulator to generate joint state estimates. In the example of FIG. 7A, at least one of the adjacent links (e.g., link L1) coupled to a particular joint (e.g., joint J1) does not have a link sensor system. The bridging estimator 442 may use a joint dynamic model of the joint J1 to generate joint state estimates of joint J1. Further, the bridging estimator 442 may use the joint dynamic models of the joint J1 and J2 to bridge the information gap between L0 and L2 caused by the lack of a link sensor system on link L1. The example of FIG. 7B illustrates joint dynamic models 752 and 754 corresponding to joints J1 and J2 respectively. As shown in FIG. 7B, the link data of the sensor 204 on L0, together with the joint dynamic model 752 for the joint J1 can be used to estimate, via inverse dynamics, the force F0 on L1 at the interface modeled by the model 752. Similarly, the link data of the sensor 204 on L2, together with the joint model of J2 754 can be used to estimate, via inverse dynamics, the force F2 on L1 at the interface modeled by the model 754. Subsequently, with known external forces on the interfaces models by the models 752 and 754, the link motion state of L1 may be computed using forward dynamics.

In some examples, the joint dynamic model may be generated based on various dynamic properties of the manipulator 202, including, for example, mass properties of the links, transmission stiffness, friction, damping, and other dynamic properties. The bridging estimator 442 may compute joint state (e.g., velocity, acceleration) estimates for joint J1 based on the joint dynamic model. Specifically, the bridging estimator 442 may compute joint state estimates based on the torque applied to the associated joint motor in a previous time step by solving the forward dynamics for joint J1.

In some embodiments, the bridging estimator 442 may also use the dynamic models of the joints J1 and J2 to bridge the information gap of L1 caused by the lack of a link sensor system thereon for the recursive kinematics estimator 440. As illustrated in the example of FIG. 7B, the bridging estimator 442 may determine states (pose, velocity, acceleration) of a fictitious link sensor system 702 located on link L1 connecting joints J1 and J2. Such a fictitious link sensor system 702 does not include any physical elements, and may also be referred to as a non-physical link sensor system 702. On the other hand, the link sensor systems 204 may also be referred to as physical link sensor system 204. Because the link L1 does not have a link sensor system 204, the bridging estimator 442 provides link data (e.g., link angular velocity data, link acceleration data) associated with that fictitious link sensor system 702 of link L1. Such link data of the fictitious link sensor system 702 on link L1 may be determined by computing the forces imparted on link L2 at an interface 756 between the joint dynamic model 752 of joint J1 and the link L1 and an interface 758 between the joint dynamic model 754 of joint J2 based on link data of links L0 and L2.

After the fictitious link sensor system 702 of link L1 is provided by the bridging estimator 442, the recursive kinematics estimator 440 may generate a joint state estimate for joint J2 using the link data of the link L1 (from the fictitious link sensor system 702) and link L2 (from the link sensor system 204) as discussed above based on equations (8), (9), and (10). Specifically, the recursive kinematics estimator 440 may generate a differential motion of adjacent links L1 and L2 based on the link data of the link L1 (from the fictitious link sensor system 702) and link L2 (from the link sensor system 204), and generate the joint state estimate for joint J2 by transforming that differential motion to the joint space of joint J2.

In some embodiments, the link state estimate of the link L1 (e.g., link data provided by the fictitious link sensor system 702) may be determined based on combining a forward link state estimate of the link L1 and a backward link state estimate of the link L1. For example, a forward link state estimate of the link L1 may be determined by forward propagating kinematics based on the link data of the link L0 and an initial joint state estimate of the joint J1. The initial joint state estimate of the joint J1 may be computed by solving forward dynamics based on a force on the joint J1 and a dynamic model of the joint J1. For further example, a backward link state estimate of the link L1 may be determined by backward propagating kinematics based on the link data of the link L2 and an initial joint state estimate of the joint J2. The initial joint state estimate of the joint J2 may be computed by solving forward dynamics based on a force on the joint J2 and a dynamic model of the joint J2.

In some embodiments, the joint state estimates of the joints J1 and J2 may be updated based on the link state estimate of the link L1 (e.g., determined based on the initial joint state estimates of the joints J1 and J2). For example, a joint state estimate for the joint J1 may be determined based on the link state estimate of the link L1 and the link data of the link L0. For further example, a joint state estimate for the joint J2 may be determined based on the link state estimate of the link L1 and the link data of the link L2.

In those embodiments, because the bridging estimator 442 uses the dynamic model to compute joint state estimates, control system performance may be improved by providing a more accurate dynamic model. Accordingly, in embodiments where the number of link sensor systems is less than the total number of links of a manipulator, the performance of the control system is improved by configuring the locations of the link sensor systems based on the difficulty of modeling the links and joints of the manipulator 202. In an example, the manipulator 202 may be configured to have the link sensor systems attached to the links or joints that are more difficult to model.

Referring to FIG. 4, in some embodiments, a weighting block 434 of the joint control unit 400 may apply different weights to joint state estimates 432 of different joints received from the joint state estimator 430. The joint state estimates 432 include, for example, joint acceleration estimates, joint velocity estimates, and/or joint pose estimates of the manipulators. By weighting the joint state estimates of the joints, the vibration at one or more control points (e.g., a tool tip 262 and/or a remote center 256) is further reduced. Various weighting schemes, including weighting schemes based on various weighting scheme parameters including, for example, joint inertias, joint physical compliances, joint distances to one or more control points, may be used. In some examples, the joint inertia includes the sum of reflected motor inertia and the total inertia of the manipulator distal to the joint. In some examples, the weighting scheme parameters may depend on and accordingly updated based on the configuration of the manipulator assembly, including, for example, the tool attached to the manipulator. In an example, a new tool including an endoscopic imaging system may replace an old tool attached to the manipulator, where the new tool is heavier than the old tool. After the tool replacement, the weighting block 434 may generate new weights based on the updated weighting scheme parameters corresponding to the manipulator with the new tool, and assign the new weights to the joint state estimates to generate updated weighted joint state estimates.

In some embodiments, the weighting block 434 includes an inertia block 444 that applies weights based on corresponding joint inertia. For a given control point (e.g., a tool tip 262 or a remote center 256), the inertia block 444 applies weights to the joint state estimates 432 based on the corresponding joint inertias. In some embodiments, the joint inertias are dependent on the configuration of the manipulator assembly 200. As such, the inertia block 444 may dynamically adjust the weights based on the configuration of the manipulator assembly 200. For example, the inertia block 444 receives first and second joint state estimates associated with first and second joints respectively, and applies first and second weights to the first and second joint state estimates respectively. In that example, the first weight is less than the second weight because the joint inertia of the first joint is less than that of the second joint. In various embodiments, the relationship between the weights and the corresponding joint inertias may be linear or nonlinear.

In some embodiments, the weighting block 434 includes a physical compliance block 446. For a given control point (e.g., a tool tip 262 or a remote center 256), the physical compliance block 446 apply weights to joint state estimates 432 based on the corresponding joint physical compliances. As such, the physical compliance block 446 may change the weights based on the configuration of the manipulator assembly 200. For example, the physical compliance block 446 receives first and second joint state estimates associated with first and second joints respectively, and applies first and second weights to the first and second joint state estimates respectively. In that example, the first weight is less than the second weight because the physical compliance of the first joint is less than that of the second joint. In various embodiments, the relationship between the weights and the corresponding physical compliances may be linear or nonlinear.

In various embodiments, the weighting block 434 may generate the weights based on the inertia, compliance, and damping of a portion of or the entire manipulator assembly, including the joints, links, and the tool. A modal weighting block 450 of the weighting block 434 may identify modal parameters (e.g., vibration frequencies and damping ratios of various vibrational modes) of the manipulator assembly (e.g., using experimental modal analysis). The modal weighting block 450 may determine the modal mass, stiffness, and damping, and then transform them to the joint actuator/joint space. The modal weighting block 450 may determine the contribution of each joint to a given vibrational mode (e.g., using a modal matrix), and determine the weights based on the contribution of a given joint to a particular vibrational mode (e.g., a fundamental vibrational mode). In an example, a larger weight is assigned to joint state estimates of a joint that has a higher contribution to a particular vibrational mode. Below is an example of a modal matrix Ψ for a 4-DOF manipulator system with 4 vibrational modes, where rows one through four corresponds to joints J1, J2, J3, and J4 (and their DOFs) respectively, and each column corresponds to a vibrational mode:

$$\Psi = \begin{bmatrix} 1.0 & 1.0 & 1.0 & 1.0 \\ 0.4 & 0.4 & 4 & 3.4 \\ 0.03 & 0.1 & 0.4 & -3.9 \\ -0.02 & -0.06 & 3 & -0.02 \end{bmatrix}.$$

In an example, the chosen mode corresponds to column 1 (e.g., a fundamental mode) of the modal matrix Ψ, then the weight for joint J1 with the $1^{st}$ DOF is higher than the weights for other joints because the corresponding matrix element ("1.0") has the largest absolute value. In another example where the chosen mode corresponds to column 4, the weight for joint J3 with the $3^{rd}$ DOF is higher than the weights for the other joints because the corresponding matrix element ("−3.9") has the largest absolute value. In a particular example, the weighting block 434 may use a scaled version of the normalized Eigenvector of the modal matrix Ψ as the weight vector for the corresponding joints.

As illustrated in FIG. 4, an integrator 438 of the joint control unit 400 receives the weighted joint state estimates 436 from the weighting block 434, and receives joint encoder data 424 from joint encoders 422. The integrator 438 may perform an integration to generate actual joint state estimates 406 $\tilde{\Theta}_{act}$ based on the joint encoder data 424 (including joint position and velocity measurement data) and the weighted joint state estimates 436 (e.g., joint velocity estimates and joint acceleration estimates). The actual joint state estimates 406 $\tilde{\Theta}_{act}$ may also be referred to as integrated joint state estimates 406. In an example, the integrator 328 may use Kalman filter to perform the integration. The integrator 328 may then provide the actual joint state estimates 406 $\tilde{\Theta}_{act}$ to the comparator 404.

Figure 8:
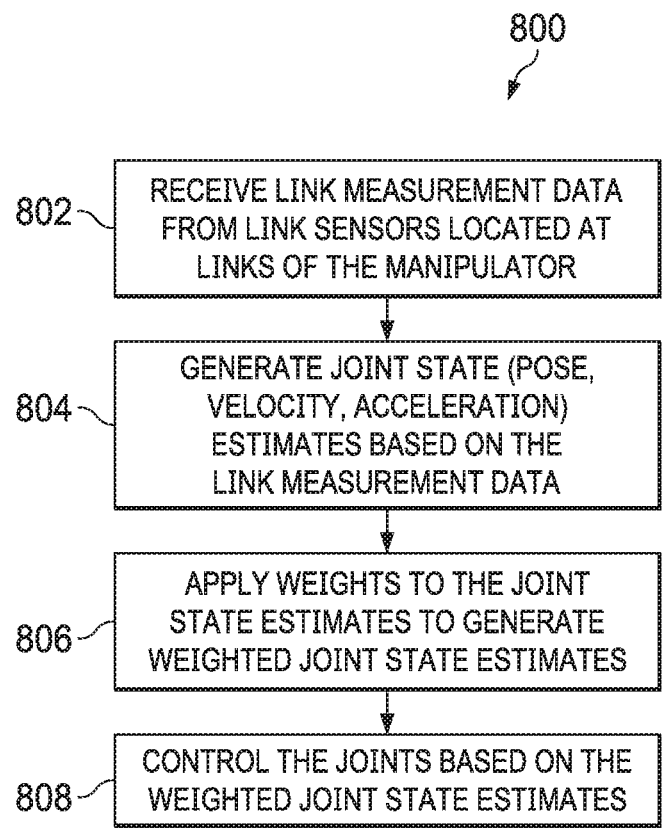
FIG. 8 is a flowchart providing a method for controlling a manipulator and an associated tool according to an embodiment of the present disclosure.

FIG. 8 illustrates a method 800 for controlling the manipulator and associated medical tool based on joint acceleration estimates of joints of the manipulator. The method 800 is illustrated in FIG. 8 as a set of processes 802 through 808 (also called operations 802 to 808). Not all of the illustrated processes 802 through 808 may be performed in all embodiments of method 800. Additionally, one or more processes that are not expressly illustrated in FIG. 8 may be included before, after, in between, or as part of the processes 802 through 808. In some embodiments, one or more of the processes may be implemented, at least in part, in the form of executable code stored on non-transitory, tangible, machine-readable media that when run by one or more processors (e.g., the processors of control system) may cause the one or more processors to perform one or more of the processes.

As shown in the method 800, a joint controller may control the movement of the joints of a manipulator based on joint acceleration estimates of joints of a manipulator. By using such joint acceleration estimates, the manipulator assembly is more responsive to acceleration transients (e.g., caused by link vibrations). To further reduce the vibrations at a given control point (e.g., a tool tip, a remote center), various weighting schemes may be applied to the joint acceleration estimations (e.g., based on joint inertias, joint physical compliances, and joint distances to a control point). Furthermore, the joint acceleration estimates are generated based on link angular velocity data, link acceleration data, or a combination thereof. In an example, by using a fused joint acceleration estimate generated based on both link angular velocity and acceleration data, robustness and signal-to-noise ratio (SNR) of the fused signal may be improved.

The method 800 begins at process 802, where a joint state estimator receives link data from link sensor systems located on links of a manipulator. In the example of FIG. 4, a joint state estimator 430 of a joint control unit 400 receives link measurement data 426 from link sensor systems 204 located on links of a manipulator 202. The link measurement data 426 may include link angular velocity data or link acceleration data.

The method 800 may then proceed to process 804, where the joint state estimator generates joint state (e.g., pose, velocity, acceleration) estimates based on the link data on adjacent links. In the example of FIG. 4, the joint state estimator 430 generates joint state estimates 432 based on the link measurement data 426. Various estimators (e.g., the recursive kinematics estimator 440, fused estimator 441, model-based bridging estimator 442, redundant sensing estimator 428, any other suitable estimator, and/or a combination thereof) may be used to generate the joint state estimates 432.

At process 804, in examples where each of the adjacent links coupled to a particular joint has a link sensor system, a recursive kinematics estimator 440 of the joint state estimator 430 may generate the joint state estimates 432 of that particular joint based on the link data based on recursive kinematics as described above with reference to FIGS. 4, 5A, and 5B.

At process 804, in examples where at least one of adjacent links coupled to a particular joint does not have a link sensor system, a bridging estimator 442 of the joint state estimator 430 may generate the joint state estimates 432 of that particular joint based on the link data of links not connected to that particular joint. In an example, the bridging estimator 442 of the joint state estimator 430 generates the joint state estimates 432 using a joint dynamic model of that particular joint.

The method 800 may proceed to process 806, where weights are applied to the joint state estimates to generate weighted joint state estimates. In the example of FIG. 4, a weighting block 434 may use various weighting schemes to apply weights to the joint state estimates. For example, an inertia block 444 may apply weights based on the corresponding joint inertias. For further example, a physical compliance block 446 may apply weights based on the physical compliance of the corresponding joints. In yet another example, a distance block 448 may apply weights based on the corresponding joint/link distances to a control point. In yet another example, a modal weighting block 450 may apply weights based modal parameters of the manipulator assembly. In some embodiments, different weights may apply to the joint acceleration estimate and joint velocity estimate in the same joint state estimate for a particular joint. In other embodiments, different weighting schemes may be applied to joint acceleration estimates and joint velocity estimates of the joints. For example, a joint inertia weighting scheme may be applied to the joint acceleration estimates, while a physical compliance weighting scheme may be applied to the joint velocity estimates.

The method 800 may then proceed to block 808, where the motion of the joints is controlled based on the weighted joint state estimates. In the example of FIG. 4, the integrator 438 generates integrated joint state estimates 406 by integrating joint encoder data 424 and the weighted joint state estimates 436. Joint feedback errors 410 are generated by comparing the desired joint state data 402 and integrated joint state estimates 406. A feedback controller 412 generates a slave torque command signal 414, which is sent to the slave manipulator 202 to drive motors of the joints. As such, the motion of the joints is controlled based on the weighted joint state estimates 436.

Figure 9:
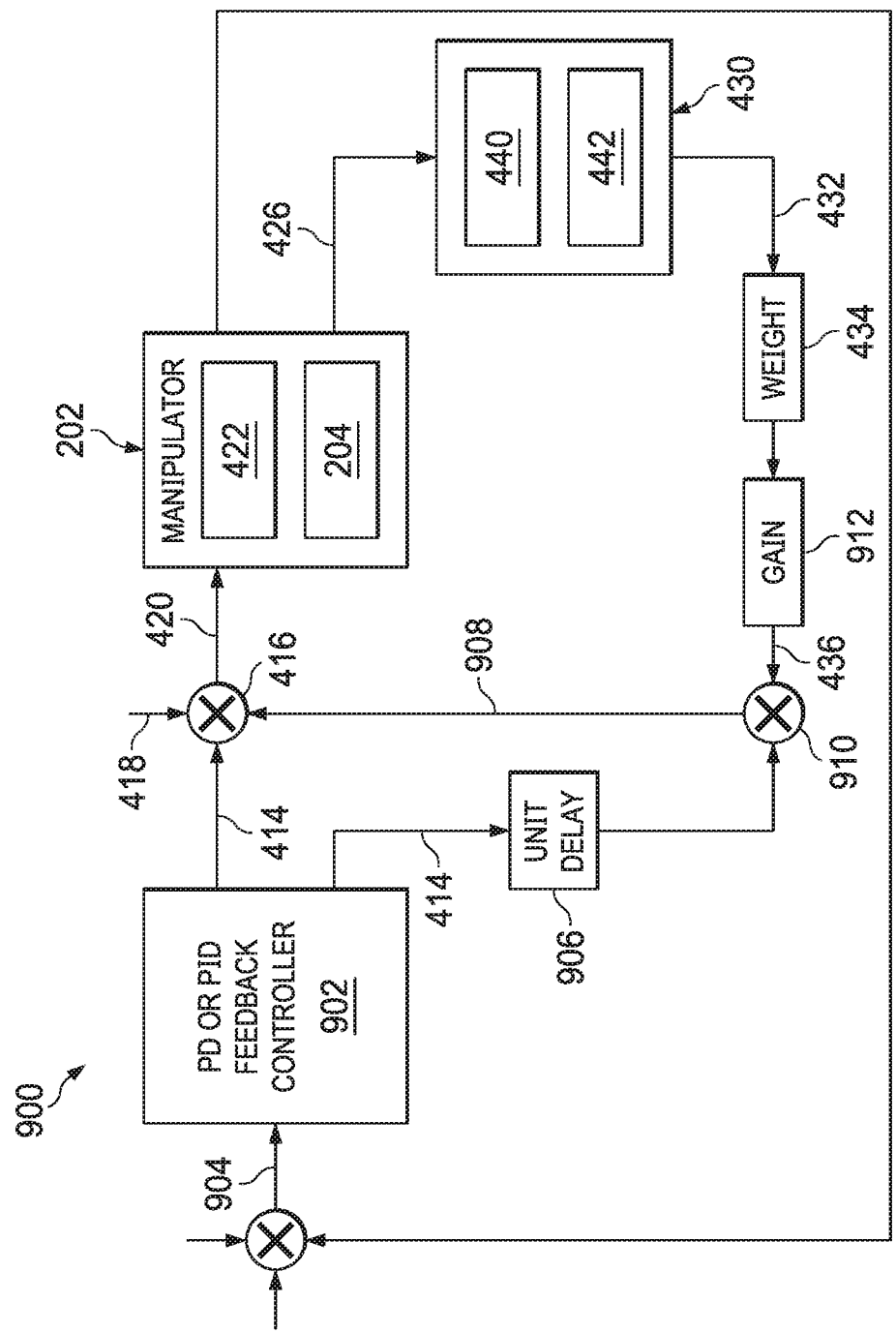
FIG. 9 illustrates a block diagram of a slave joint controller in accordance with an embodiment of the present disclosure.

Referring to FIG. 9, in some embodiments, a joint controller may use a proportional-derivative (PD) or proportional-integral-derivative (PID) feedback controller that does not include an acceleration term A. In those embodiments, joint acceleration errors generated based on link data may be treated as a torque adjustment in the joint controller. In some embodiments, a torque adjustment 908 is generated based on weighted joint state estimates 436. A joint state estimator 430 generates joint state estimates 432 based on link measurement data 426 provided by link sensor systems located on links of the manipulator 202. A gain block 912 and a weighting block 434 may apply gains and weights to the joint state estimates 432, and generate weighted joint state estimates 436. A comparator 910 receives the weighted joint state estimates 436, compares the weighted joint state estimates 436 to the desired feedback torque of a previous time step. The desired feedback torque of a previous time step is provided by a unit delay block 906 by applying a delay to the desired feedback torque in a slave torque command signal 414.

In some embodiments, the torque adjustment 908 is applied to a slave torque command signal 414 to generate an adjusted slave torque command signal 420 for controlling the joints of the manipulator 202. In the example of FIG. 9, a joint controller 900 includes a feedback controller 902 (e.g., a PD or PID feedback controller) that does not include an acceleration term A. The feedback controller 902 handles joint errors 904 (e.g., joint position error, joint velocity error), and generates a slave torque command signal 414. The slave torque command signal 414 is sent to a combiner 416, which adjusts the slave torque command signal 414 based on disturbance torque value 418 and torque adjustment 908 to generate an adjusted slave torque command signal 420. The adjusted slave torque command signal 420 may be sent to the slave manipulator 202, and be used to drive motors (e.g., motors for joints J1, J2, J3, J4) of the slave manipulator 202.

Figure 10:
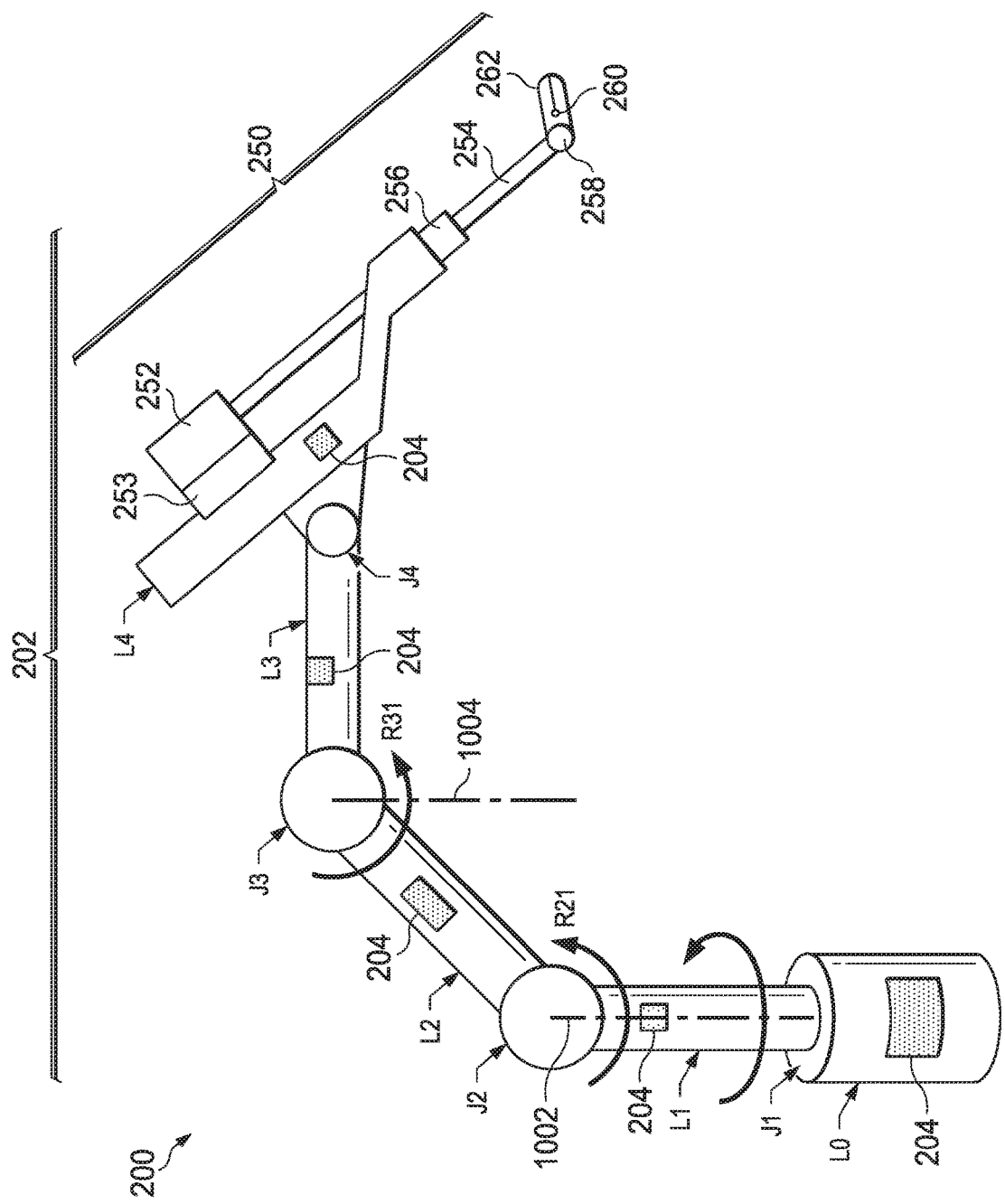
FIG. 10 illustrates a robotic manipulator assembly with link sensor systems in accordance with an embodiment of the present disclosure.

Referring to FIG. 10, in some embodiments, the kinematic estimator may compute joint state estimates in directions that are not controllable by the nearest proximal joint. These will be referred to as residual joint state estimates including residual joint velocity estimates (also referred to as residual velocity) and residual joint acceleration estimates (also referred to as residual acceleration). In an example, if the $\hat{Z}_1$ and $\hat{Z}_2$ are active axes (i.e. with actuators capable of controlling motion about those axes) and $\hat{Z}_3$ is a passive axis, then the joint state estimates computed about $\hat{Z}_3$ are referred to as residual joint state estimate or residual.

As shown in the example of FIG. 10, by using link sensor systems located on the links of a manipulator, a control system may determine that residual accelerations at the joints are in line with a proximal joint of the manipulator. The joint controller may then control a proximal actuator of the proximal joint to control those distally observable residual accelerations. In the example of FIG. 10, a manipulator 202 includes joints J1, J2, J3, and J4 and links L1, L2, L3, and L4. Joint J1 is a base roll having an axis 1002 along gravity.

In some embodiments, residual accelerations at particular joints may not be controlled locally by joint actuators of these particular joints. For example, a residual acceleration R21 at the joint J2 along the axis 1002 is not controlled locally by a joint actuator of the joint J2. For further example, a residual acceleration R31 at the joint J3 along an axis 1004 aligned with the axis 1002 is not controlled locally by a joint actuator of the joint J3.

In some embodiments, a joint controller (e.g., a joint control unit 400 of FIG. 4) may determine that those residual accelerations R21 and R31 at the joints J2 and J3 are in line with a proximal joint (e.g., joint J1) of the manipulator 202 based on link data provided by the link sensor systems 204. For example, a joint state estimator (e.g., joint state estimator 430 of FIG. 4) may generate joint acceleration estimates of joints J2 and J3. The joint controller may determine that residual accelerations R21 and R31 are aligned with joint axis 1002 of joint J1, and adjust the desired joint acceleration of J1 based on the residual accelerations R21 and R31. In an example, residual acceleration R21 has the same axis 1002 as the joint J1, and is directly in line with the joint J1. In that example, the joint acceleration estimate of J1 may be adjusted directly by the residual acceleration R21. In another example, residual acceleration R31 has an axis 1004 that is offset from the axis 1002 of joint J1. In that example, residual acceleration R31 may be transformed to the axis 1002 of joint J1 (e.g., based on equivalent end point acceleration at a tip of the manipulator assembly), and then be applied to adjust the desired joint acceleration of joint J1. The joint controller may then control the actuator of the joint J1 based on the adjusted desired joint acceleration of joint J1, which controls those distally observable residual accelerations R21 and R31.

One or more elements in embodiments of the invention may be implemented in software to execute on a processor of a computer system such as control processing system. When implemented in software, the elements of the embodiments of the invention are essentially the code segments to perform the necessary tasks. The program or code segments can be stored in a processor-readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read-only memory (ROM), a flash memory, an erasable programmable read-only memory (EPROM); a floppy diskette, a CD-ROM, an optical disk, a hard disk, or other storage device, the code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A system comprising:
a robotic manipulator including a first joint and a second joint; and
a processing unit including one or more processors, the processing unit configured to:
provide a first joint state estimate of the first joint;
provide a second joint state estimate of the second joint;
determine a first weight and a second weight for the first joint state estimate and the second joint state estimate respectively based on one or more weighting scheme parameters associated with the robotic manipulator;
apply the first weight to the first joint state estimate to generate a first weighted joint state estimate;
apply the second weight to the second joint state estimate to generate a second weighted joint state estimate; and
control the first joint and the second joint based on the first weighted joint state estimate and the second weighted joint state estimate.

2. The system of claim 1, wherein the processing unit is further configured to:
in response to a change in a configuration of the robotic manipulator, update the first and second weights based on the configuration of the robotic manipulator.

3. The system of claim 1, wherein the processing unit is further configured to:
determine the first and second weights based on at least one of a first joint inertia of the first joint and a second joint inertia of the second joint.

4. The system of claim 3, wherein the first weight is greater than the second weight, and
wherein the first joint inertia is greater than the second joint inertia.

5. The system of claim 3, wherein the first joint inertia includes a total inertia of the robotic manipulator distal to the first joint, or wherein the first joint inertia includes reflected motor inertia associated with the first joint.

6. The system of claim 1, wherein the processing unit is further configured to:
determine the first and second weights based on at least one of a first physical compliance of the first joint and a second physical compliance of the second joint.

7. The system of claim 6, wherein the first weight is greater than the second weight, and
wherein the first physical compliance is greater than the second physical compliance.

8. The system of claim 1, wherein the processing unit is further configured to:
determine the first and second weights based on at least one of a first distance between the first joint and a control point of the robotic manipulator and a second distance between the second joint and the control point.

9. The system of claim 8, wherein the first weight is greater than the second weight, and wherein the first distance is less than the second distance.

10. The system of claim 1, wherein the processing unit is further configured to:
determine the first and second weights based on at least one of a first contribution of the first joint to a first vibrational mode of the robotic manipulator and a second contribution of the second joint to the first vibrational mode of the robotic manipulator.

11. A method comprising:
generating a first joint state estimate of a first joint of a robotic manipulator;
generating a second joint state estimate of a second joint of the robotic manipulator;
determining a first weight and a second weight for the first joint state estimate and the second joint state estimate respectively based on one or more weighting scheme parameters associated with the robotic manipulator;
applying the first weight to the first joint state estimate to generate a first weighted joint state estimate;
applying the second weight to the second joint state estimate to generate a second weighted joint state estimate; and
controlling the first joint and the second joint based on the first weighted joint state estimate and the second weighted joint state estimate.

12. The method of claim 11, further comprising:
in response to a change in a configuration of the robotic manipulator, updating the first and second weights based on the configuration of the robotic manipulator.

13. The method of claim 11, further comprising:
determining the first and second weights based on at least one of a first joint inertia of the first joint and a second joint inertia of the second joint.

14. The method of claim 13, wherein the first weight is greater than the second weight, and
wherein the first joint inertia is greater than the second joint inertia.

15. The method of claim 13, wherein the first joint inertia includes a total inertia of the robotic manipulator distal to the first joint, or wherein the first joint inertia includes reflected motor inertia associated with the first joint.

16. The method of claim 11, further comprising:
determining the first and second weights based on at least one of:
a first physical compliance of the first joint and a second physical compliance of the second joint.

17. The method of claim 11, further comprising:
determining the first and second weights based on at least one of a first physical compliance of the first joint and a second physical compliance of the second joint.

18. The method of claim 17, wherein the first weight is greater than the second weight, and
wherein the first physical compliance is greater than the second physical compliance.

19. The method of claim 11, further comprising:
determining the first and second weights based on at least a first contribution of the first joint to a first vibrational mode of the robotic manipulator and a second contribution of the second joint to the first vibrational mode of the robotic manipulator.

20. A non-transitory machine-readable medium comprising a plurality of machine-readable instructions which, when executed by one or more processors, are adapted to cause the one or more processors to perform a method comprising:
generating a first joint state estimate of a first joint of a robotic manipulator;
generating a second joint state estimate of a second joint of the robotic manipulator;

determining a first weight and a second weight for the first joint state estimate and the second joint state estimate respectively based on one or more weighting scheme parameters associated with the robotic manipulator;

applying the first weight to the first joint state estimate to generate a first weighted joint state estimate;

applying the second weight to the second joint state estimate to generate a second weighted joint state estimate; and controlling the first joint and the second joint based on the first weighted joint state estimate and the second weighted joint state estimate.

\* \* \* \* \*